(12) United States Patent
Hamilton et al.

(10) Patent No.: US 7,160,316 B2
(45) Date of Patent: Jan. 9, 2007

(54) METHODS AND APPARATUS FOR ADJUSTING BODY CORE TEMPERATURE

(75) Inventors: Nathan Hamilton, Palo Alto, CA (US); John Roy Kane, Redwood City, CA (US); H. Lawson Fisher, Portola Valley, CA (US); Loren D. Titsworth, Fremont, CA (US); Barry Hickerson, Modesto, CA (US)

(73) Assignee: Dynatherm Medical, Inc., Fremont, CA (US)

(*) Notice: Subject to any disclaimer, the term of this patent is extended or adjusted under 35 U.S.C. 154(b) by 61 days.

(21) Appl. No.: 10/948,121

(22) Filed: Sep. 23, 2004

(65) Prior Publication Data

US 2005/0209663 A1 Sep. 22, 2005

Related U.S. Application Data

(60) Provisional application No. 60/505,798, filed on Sep. 24, 2003.

(51) Int. Cl.
*A61F 7/00* (2006.01)

(52) U.S. Cl. .......................... 607/111; 128/898; 607/96; 607/104

(58) Field of Classification Search .......... 607/96–114; 128/898; 2/82
See application file for complete search history.

(56) References Cited

U.S. PATENT DOCUMENTS

| 1,399,095 | A | 12/1921 | Webb, Sr. |
|---|---|---|---|
| 3,217,707 | A | 11/1965 | Werding |
| 4,186,294 | A | 1/1980 | Bender |
| 4,523,594 | A | 6/1985 | Kuznetz |
| 4,530,350 | A | 7/1985 | Brown et al. |
| 4,648,392 | A | 3/1987 | Cartier et al. |
| 4,658,823 | A | 4/1987 | Beddoe et al. |
| 5,074,285 | A | 12/1991 | Wright |
| 5,149,331 | A | 9/1992 | Ferdman et al. |
| 5,241,958 | A | 9/1993 | Noeldner |
| 5,314,455 | A | 5/1994 | Johnson, Jr. et al. |
| 5,369,807 | A | 12/1994 | Cho et al. |
| 5,441,477 | A | 8/1995 | Hargest |
| 5,478,490 | A | 12/1995 | Silver |
| 5,683,438 | A | 11/1997 | Grahn |
| 5,755,756 | A | 5/1998 | Freedman, Jr. et al. |
| 5,960,475 | A | * | 10/1999 | Fewtrell ........................ 2/82 |
| 6,149,674 | A | 11/2000 | Borders |
| 6,245,094 | B1 | * | 6/2001 | Pompei ....................... 607/104 |
| 6,277,143 | B1 | 8/2001 | Klatz et al. |

(Continued)

FOREIGN PATENT DOCUMENTS

FR 2544202 10/1984

(Continued)

OTHER PUBLICATIONS

Partial Supplementary European Search Report for European Application No. 96907933.4, dated Jul. 9, 1999.

(Continued)

*Primary Examiner*—Henry M Johnson, III
(74) *Attorney, Agent, or Firm*—Patterson & Sheridan, L.L.P.

(57) ABSTRACT

A method and apparatus for adjusting body core temperature are provided. The apparatus comprises an appendage chamber that is adapted to be disassembled from a heat exchange element. In one aspect, the appendage chamber is disposable. The appendage chamber provides a negative pressure environment for a patient's appendage placed therein. An appendage is heated and exposed to a negative pressure environment within the apparatus to efficiently raise or maintain the body core temperature of the patient.

38 Claims, 27 Drawing Sheets

U.S. PATENT DOCUMENTS

| | | | |
|---|---|---|---|
| 6,286,144 B1* | 9/2001 | Henderson et al. | 2/69 |
| 6,461,379 B1 | 10/2002 | Carson et al. | |
| 6,602,277 B1 | 8/2003 | Grahn et al. | |
| 6,620,187 B1 | 9/2003 | Carson et al. | |
| 6,645,232 B1 | 11/2003 | Carson | |
| 6,648,905 B1 | 11/2003 | Hoglund et al. | |
| 6,656,208 B1 | 12/2003 | Grahn et al. | |
| 6,660,027 B1 | 12/2003 | Gruszecki et al. | |
| 6,669,715 B1 | 12/2003 | Hoglund et al. | |
| 6,673,099 B1 | 1/2004 | Grahn et al. | |
| 6,692,518 B1 | 2/2004 | Carson | |
| 6,699,267 B1 | 3/2004 | Voorhees et al. | |
| 6,748,609 B1* | 6/2004 | Garigan | 2/457 |
| 6,846,322 B1* | 1/2005 | Kane et al. | 607/111 |
| 6,966,922 B1* | 11/2005 | Grahn et al. | 607/104 |
| 2002/0007201 A1* | 1/2002 | Grahn et al. | 607/104 |
| 2002/0019653 A1* | 2/2002 | Grahn et al. | 607/96 |
| 2002/0022871 A1* | 2/2002 | Grahn et al. | 607/108 |
| 2003/0024684 A1 | 2/2003 | Lyons et al. | |
| 2003/0040783 A1* | 2/2003 | Salmon | 607/111 |
| 2004/0127964 A1* | 7/2004 | Grahn et al. | 607/108 |
| 2004/0133253 A1* | 7/2004 | Grahn et al. | 607/96 |
| 2004/0158303 A1* | 8/2004 | Lennox et al. | 607/109 |
| 2004/0225341 A1* | 11/2004 | Schock et al. | 607/104 |
| 2005/0085882 A1* | 4/2005 | Grahn et al. | 607/104 |
| 2005/0096714 A1* | 5/2005 | Freedman et al. | 607/104 |

FOREIGN PATENT DOCUMENTS

| | | |
|---|---|---|
| WO | WO 96/28120 | 9/1996 |
| WO | WO 98/40039 | 9/1998 |
| WO | WO 01/80790 | 11/2001 |
| WO | WO 02/085266 A1 | 10/2002 |
| WO | WO 03/045289 | 6/2003 |

OTHER PUBLICATIONS

Partial Supplementary Search Report for European Application No. 98911542.3, dated Apr. 7, 2000.

International Preliminary Search Report for International Application No. PCT/US02/37432, dated Feb. 2, 2004.

Dennis Grahn, et al., "Recovery From Mild Hypothermia Can Be Accelerated By Mechanically Distending Blood Vessels in the Hand," *American Physiological Society*, Jul. 6, 1998, pp. 1643-1648.

Eldar Soreide, et al., "A Non-Invasive Means to Effectively Restore Normothermia in Cold Stressed Individuals: A Preliminary Report," *The Journal of Emergence Medicine*, 1999, pp. 725-730, vol. 17, No. 4, U.S.A.

Dennis Grahn, "Hypothermia in Trauma-Deliberate or Accidental," Trauma Care '97, 10th Annual Trauma Anesthesia and Critical Care Symposium and World Exposition, May 15-17, 1997, pp. i and 1-21, Baltimore.

Michael Mcewan, "Hypothermia—Physiology, Signs, Symptoms and Treatment Considerations," Search and Rescue Society of British Columbia, www.sarbc.org/hypo1.html, Oct. 28, 1995, pp. 1-6.

"NCI Fact Sheet: Hyperthermia in Cancer Treatment," Immune Institute, www.immuneinstitute.com/hyperthermia.htm, Jun. 1999, pp. 1-2.

PCT International Search Report and Written Opinion for PCT/US2004/031116, dated Jan. 24, 2005. (DYNA/0002.PC.).

* cited by examiner

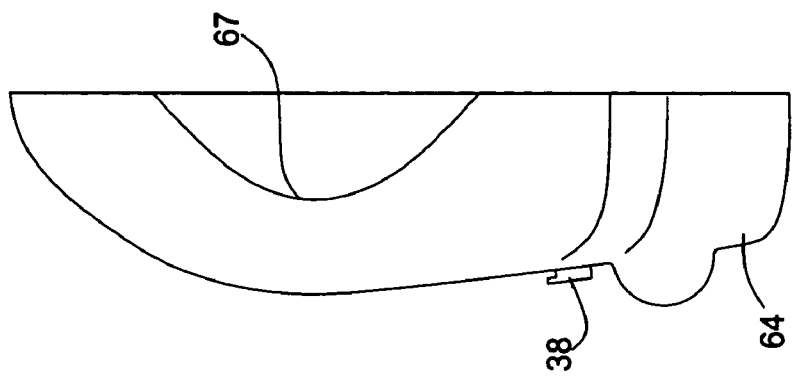
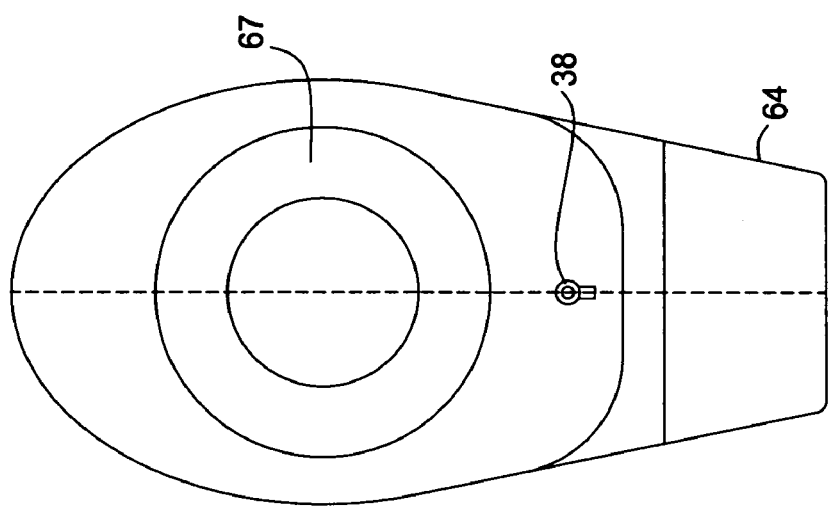
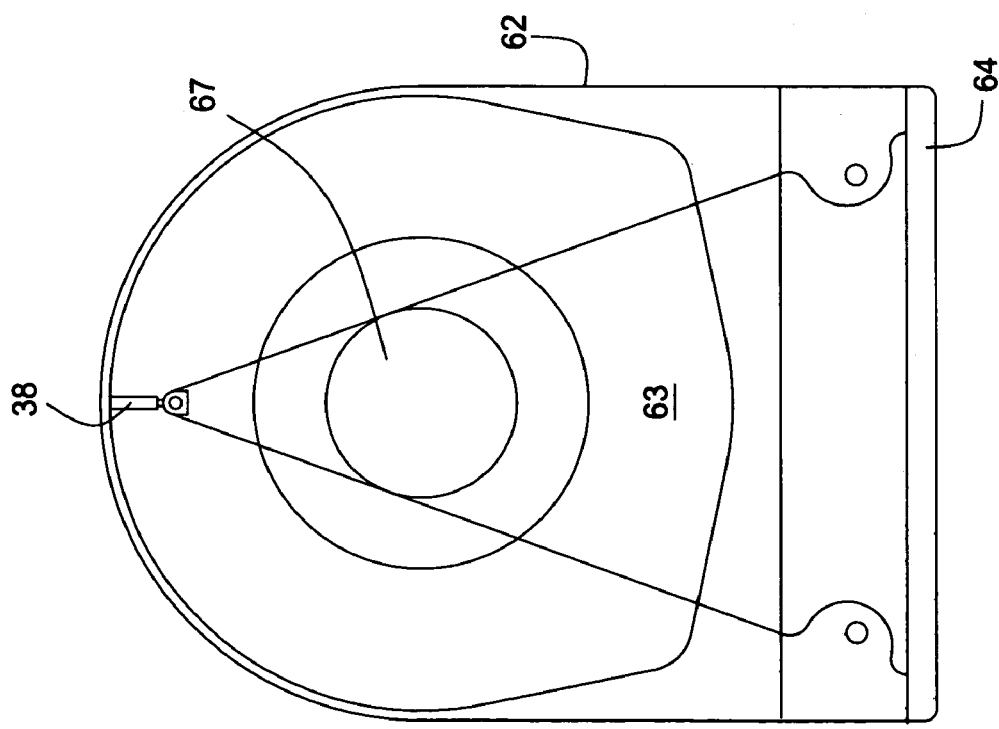

METHODS AND APPARATUS FOR ADJUSTING BODY CORE TEMPERATURE

CROSS-REFERENCE TO RELATED APPLICATIONS

This application claims priority to U.S. provisional Patent Application Ser. No. 60/505,798, filed Sep. 24, 2003, which is herein incorporated by reference.

BACKGROUND OF THE INVENTION

1. Field of the Invention

Embodiments of the invention generally relate to a method and apparatus for affecting a body's core temperature. In particular, embodiments of the invention relate to elevating and/or maintaining a body's core temperature.

2. Description of the Related Art

The human body possesses a complex mechanism for regulating its core temperature. Core body temperature is the temperature of the core vital organs such as the heart, lungs, liver, and kidneys, whereas surface temperature is the temperature of the superficial skin and fat. The primary means of core temperature regulation are through specialized vascular structures called arteriovenous anastomoses (AVAs) located in the palms of the hands and the soles of the feet. AVAs are blood vessels that connect arteries and veins and act as shunts to bypass blood flow from nutritional capillary beds, such as when a body is overheating. However, in response to cold temperatures, these vascular structures will constrict, forcing blood back toward the body core. As a result, one of the symptoms people in cold conditions usually experience is coldness in their hands and feet. When an individual experiences hypothermia, blood flow to the extremities drops by nearly 90%.

As defined herein, hypothermia is a subnormal body core temperature. Hypothermia may occur when the body's temperature control mechanisms are overwhelmed by extreme external cold conditions or medically compromised such as by anesthesia. Under such conditions, the body loses more heat than it can produce and its core temperature begins to drop.

Hypothermia may be caused by exposure to extremely cold temperatures, prolonged exposure to cold temperatures, or by indirect causes such as trauma to the body or the use of an anesthetic. Anesthetics may reduce the body's ability to produce heat as well as affect the way the body regulates temperature. For example, during anesthesia, patients generally lose the ability to shiver which is one of the body's ways of generating heat. Furthermore, anesthetics reduce the body's ability to constrict blood vessels, which is one of the primary methods the body uses to conserve heat.

One way to treat hypothermia is core re-warming. In order to counter the clinical consequences of hypothermia, the vital organs must be warmed to physiological temperature. Traditional devices for treating hypothermia such as warming blankets or warm liquid baths are slow and generally ineffective in treating hypothermia. These treatments merely warm the superficial skin and fat. Since the blood flow to the extremities in hypothermic patients is severely reduced, the blood flow is incapable of efficiently conducting heat to the body's core. Current non-invasive treatments for re-warming hypothermic patients typically offer a heating rate of <1 degree Celsius per hour. Although the patient's surface temperature may increase with surface warming, the core temperature often remains low. In a post-surgical situation, this central core hypothermia can have effects on recovery and may cause post-anesthesia complications. Some advanced invasive treatments involving intravenous injection of warm fluids e.g., saline solution, are effective in quickly re-warming the body core, but require expertise and expose the patient to unnecessary risks such as infection and bleeding.

Therefore, there remains a need for an apparatus and method to adjust the body core temperature of a patient. In particular, there is a need for a non-invasive, convenient apparatus for efficiently adjusting body core temperature.

SUMMARY OF THE INVENTION

Embodiments of the invention provide methods and apparatus for adjusting body core temperature. Embodiments provide an apparatus for regulating a body core temperature comprising an appendage chamber having an appendage seal attached thereon. Embodiments also provide an apparatus for regulating a body core temperature comprising an appendage chamber having an appendage seal attached thereon, wherein the appendage chamber is adapted to be disassembled from a heat exchange element.

In further embodiments, a method of regulating a body core temperature comprises placing an appendage in an apparatus comprising an appendage chamber having an appendage seal attached thereon and a heat exchange element, and heating the appendage in a negative pressure environment.

In other embodiments, a method of regulating a body core temperature comprises placing an appendage in an apparatus comprising an appendage chamber having an appendage seal attached thereon and a heat exchange element, and heating the appendage. In one embodiment, heating the appendage comprises using between about 5 watts and about 250 watts to raise a body core temperature at a rate of between about 4° C./hour and about 12° C./hour.

In a further embodiment, a method of regulating a body core temperature comprises exposing one or more extremities of a body to negative pressure, and heating a region of the body adjacent to the one or more extremities.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 17A is a top plane view of an embodiment of a storable apparatus of the invention in an opened portion.

FIG. 17B is a plane view of an embodiment of a storable apparatus of the invention in a closed position.

FIG. 17C is a side view of an embodiment of a storable apparatus of the invention.

DETAILED DESCRIPTION OF THE INVENTION

Embodiments of the invention include an apparatus for regulating a body's core temperature and a method of treating a patient to regulate the body's core temperature. Regulating the body's core temperature may include elevating and/or maintaining the body's core temperature. The body or patient may be a human or other mammal. Generally, the apparatus includes an appendage vacuum chamber, an appendage seal, and a heat exchange element. In one embodiment, the apparatus provides a negative pressure environment that vasodilates the appendage vasculature. The vasodilation of the appendage vasculature increases the heat exchange between the appendage and the body core by increasing blood flow between the appendage and the body core.

Embodiments of the invention provide an appendage chamber that may be used to provide a negative pressure environment to appendages such as a hand, an arm, a foot, or a leg. While embodiments of the invention will be described further below with respect to a hand chamber, it is recognized that the hand chambers described below may be adapted for use with other appendages that have vasculature suitable for the vasodilation methods described herein.

Figure 1:
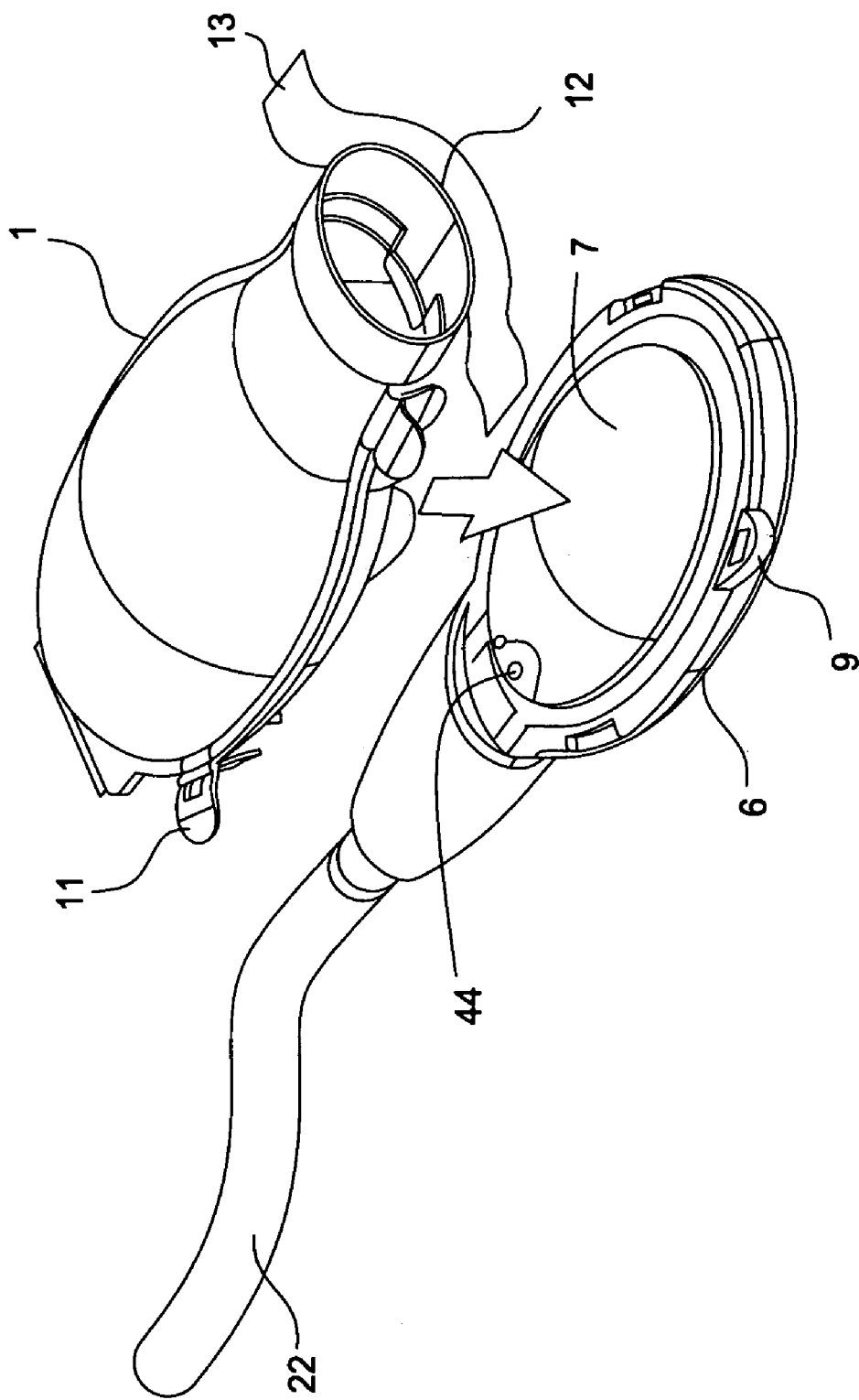
FIG. 1 is a perspective view of an embodiment of a negative pressure chamber and a heat exchange element.

FIG. 1 is a perspective view of an embodiment of a hand chamber (1) and a heat exchange element (6). The hand chamber (1) and the heat exchange element (6) provide an enclosure in which a hand may be exposed to a vacuum environment and heated. A vacuum is provided to the enclosure via vacuum ports (44) in the heat exchange element (6) that are connected to vacuum lines covered by a protective sheath (22). A hand disposed in the enclosure is secured to the hand chamber (1) by a hand seal (13) attached to the hand chamber (1) at a hand opening (12) of the hand chamber (1). The hand chamber (1) has an opening (5) (shown in FIG. 5) in its lower portion such that a hand disposed in the hand chamber (1) rests on a heat exchange surface (7) of the heat exchange element (6), which protrudes through the opening in the hand chamber (1). The hand chamber (1) and the heat exchange element (6) may be connected by fasteners, such as fasteners (9) on the heat exchange element (6) that mate with the hand chamber (1). The fasteners between the hand chamber and the heat exchange element are adapted to allow disassembly of the apparatus by allowing disengagement of the hand chamber from the heat exchange element. The hand chamber (1) may also include fasteners, such as fasteners (11), to connect an upper housing and lower housing of the hand chamber, as described below with respect to FIGS. 5 and 6. Additional aspects of the hand chamber (1) and additional embodiments of hand chambers will also be described below.

Figure 2:
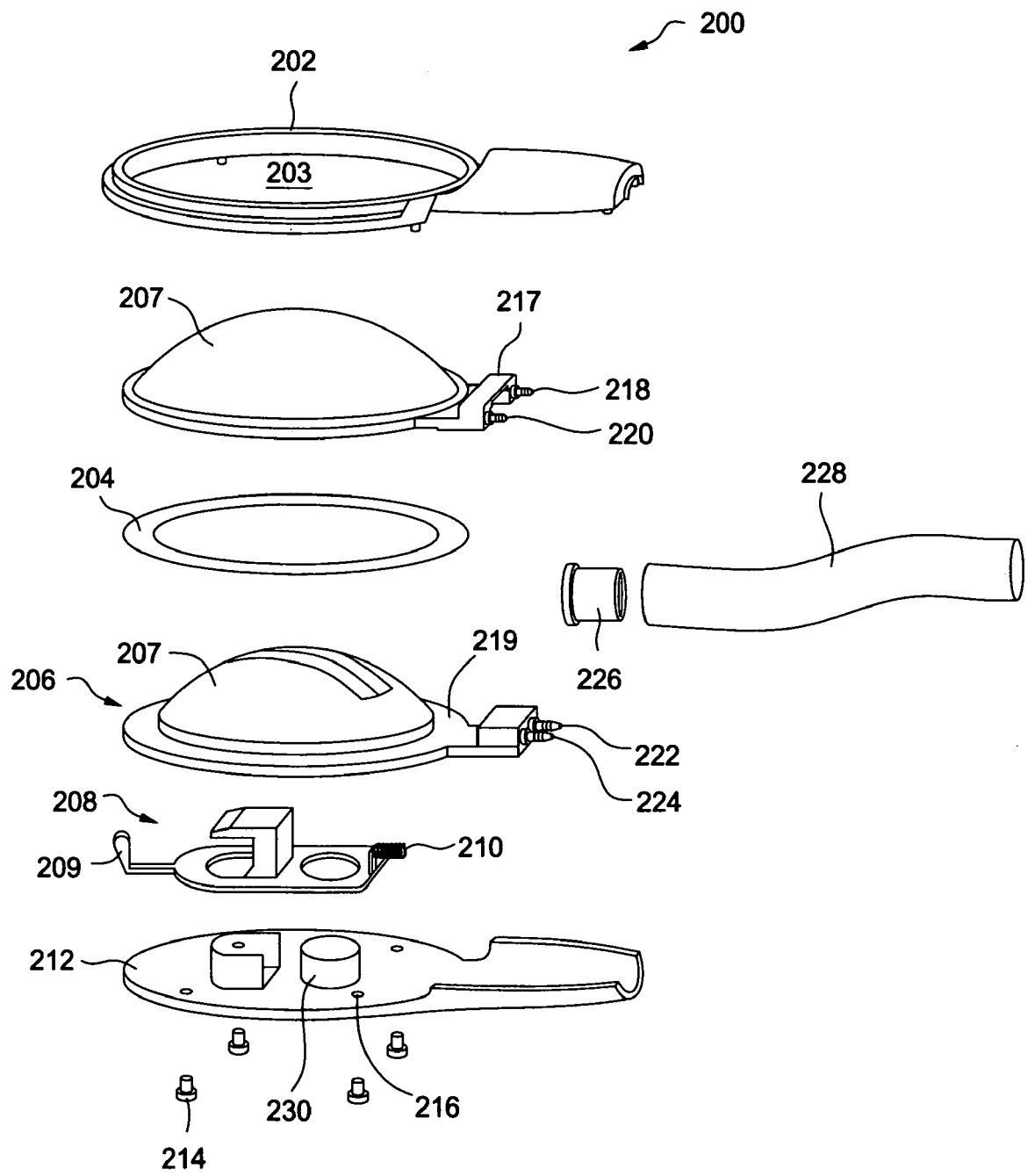
FIG. 2 is side exploded view of another embodiment of a heat exchange element.

The heat exchange element of embodiments of the invention generally provides a heat exchange surface that heats a hand placed thereon. FIG. 2 is an exploded view of one embodiment of a heat exchange element. Heat exchange element (200) comprises a top cover (202) defining a central aperture (203) through which heat exchange surface (207) projects. Heat exchange surface (207) may be an aluminum dome, for example. Vacuum ports (218) and (220) are attached to a base (217) of the heat exchange surface (207). In one embodiment, one of the vacuum ports (218) or (220) is a port for a line that provides a vacuum therethrough for the enclosure defined by the hand chamber and the heat exchange element and the other vacuum port is a port for a line that senses the vacuum conditions provided by the vacuum line. A gasket (204) separates the heat exchange surface (207) and heat exchange medium circulator (206), which may comprise a plastic surface. Heat exchange media ports (222) and (224) are attached to a base (219) of heat exchange medium circulator (206). The vacuum connections (218) and (220) and the heat exchange media ports (222) and (224) are surrounded by a connector (226) that attaches to tubing (228) that contains the lines that connect the vacuum ports (218) and (220) to a vacuum source and the heat exchange media ports (222) and (224) to a heat source.

Figure 8:
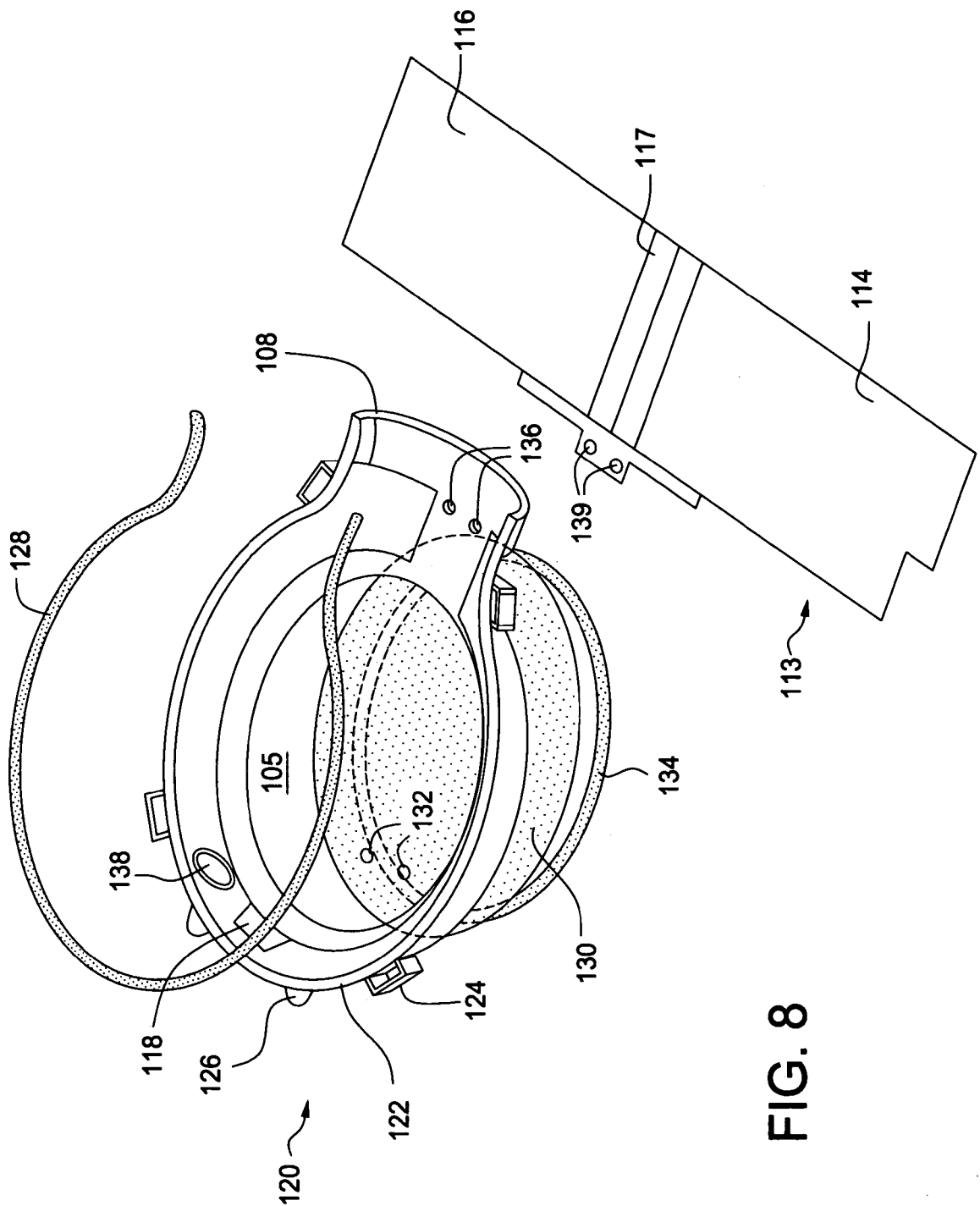
FIG. 8 is a top exploded view of a lower portion of a negative pressure chamber of another embodiment of the invention.

The heat exchange element (200) further comprises a movable portion (208) comprising one or more protruding regions (209) that mate with one or more recessed regions (118) of the lower body portion (122) of the hand chamber (shown in FIG. 8). The protruding regions (209) are retracted from the recessed regions (118) by activating spring (210) of the movable portion (208) such that the heat exchange element (200) is detached from the hand chamber. The spring (210) is activated by a switch (230), such as a pinch release switch, located in the bottom cover (212) of the heat exchange element (200). The movable portion (208) is attached to a bottom cover (212) of the heat exchange element (200) by fasteners (214) disposed through holes (216) in the bottom cover (212).

Figure 3A:
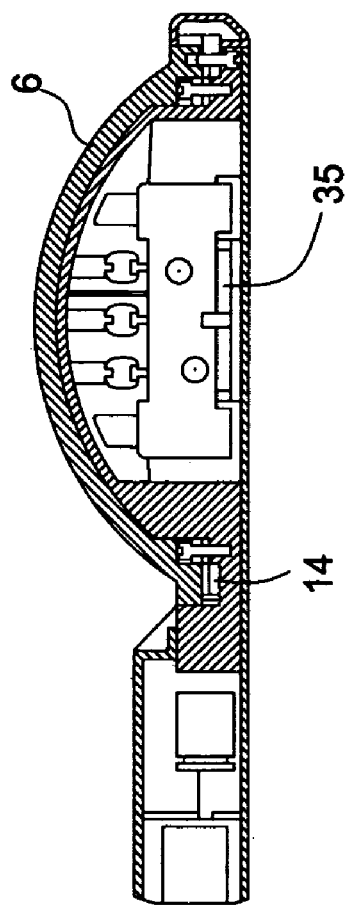
FIG. 3A is a cross-sectional view of the heat exchange element shown in FIG. 3.
Figure 3:
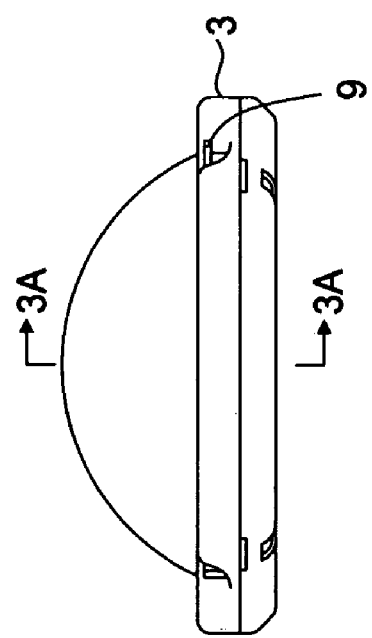
FIG. 3 is a side view of another embodiment of a heat exchange element.

FIGS. 3 and 3A illustrate an embodiment of a heat exchange element comprising a spring loaded tong engagement that is controlled by an actuator, which may be a lever, button, or pinch switch. In one aspect, the spring loaded tong engagement is an example of a movable portion (208) of a heat exchange element (200), as described above with respect to FIG. 2. The actuator may be located at any convenient location. For example, as shown in FIG. 3, actuator (35) may be a pinch release switch situated at the bottom of the heat exchange element (6). The actuator (35) pulls the fasteners (9), which may be spring loaded tongs, back into the heat exchange element (6) to release the hand chamber from the heat exchange element.

FIG. 3A also shows an optional flexible diaphragm (14) within the heat exchange element (6). In one embodiment, the heat exchange surface and chamber contacting surface of the heat exchange element (6), which are preferably made of aluminum and mounted on the flexible diaphragm (14), may be forced against the hand chamber using pressure from the heat exchange medium being pumped into the heat exchange element (6). In this embodiment, the heat exchange surface, i.e., the hand contacting surface, is preferably dome shaped. Once this pressure is applied, the heat exchange surface is generally free to move upward relative to the chamber engagement tongs, increasing the pressure against the chamber contacting surface that mates with the hand chamber. For instance, if the area of the heat exchange surface is 25 inches (5" by 7" ellipse), and the heating medium pressure is 3 psi, then the extra clamping force totals 75 pounds, distributed over the interface or seal between the heat exchange element and the chamber. In a variation of this embodiment (not shown), a rigid heat exchange surface could move upward freely with heating medium pressure if it were mounted with a piston type seal to the body of the heat exchanger. Again, the purpose would be to increase the sealing pressure against the chamber.

In any of the embodiments described herein, the heat exchange element may be heated by air, liquid, peltier devices, radiant methods, electrical methods, or chemical heating or cooling methods. As defined herein, a heat exchange medium is any substance, such as a gas or liquid, that may be used to heat the heat exchange surface of the heat exchange element. For instance, the heat exchange surface may be warmed by hot air as a heat exchange medium circulated within the heat exchange element.

Figure 4:
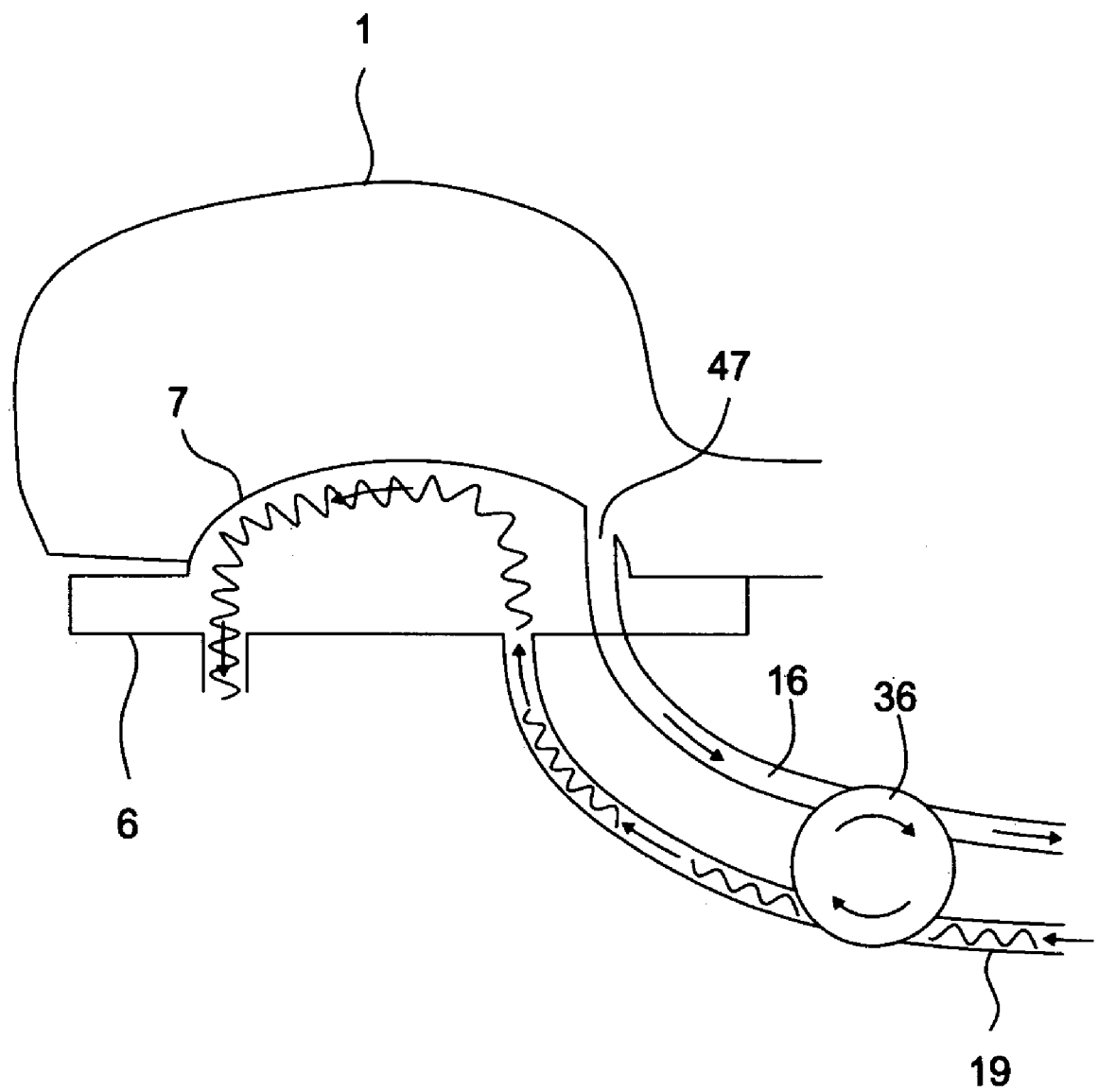
FIG. 4 is a side, cross-sectional schematic of another embodiment of the invention including a negative pressure chamber and a heat exchange element.

FIG. 4 is a schematic, cross-sectional view of another embodiment of the invention including a hand chamber and a heat exchange element. In this embodiment, hot air is introduced into the heat exchange element (6) through a heat exchange medium line (19). A vacuum may be applied to the hand chamber (1) by a turbo driven impeller (36) attached to a hot air fan source (not shown) by vacuum line (16), or driven by the venturi effect as hot air rushes past vacuum port (47) in the chamber (1), as shown in FIG. 4.

Figure 5:
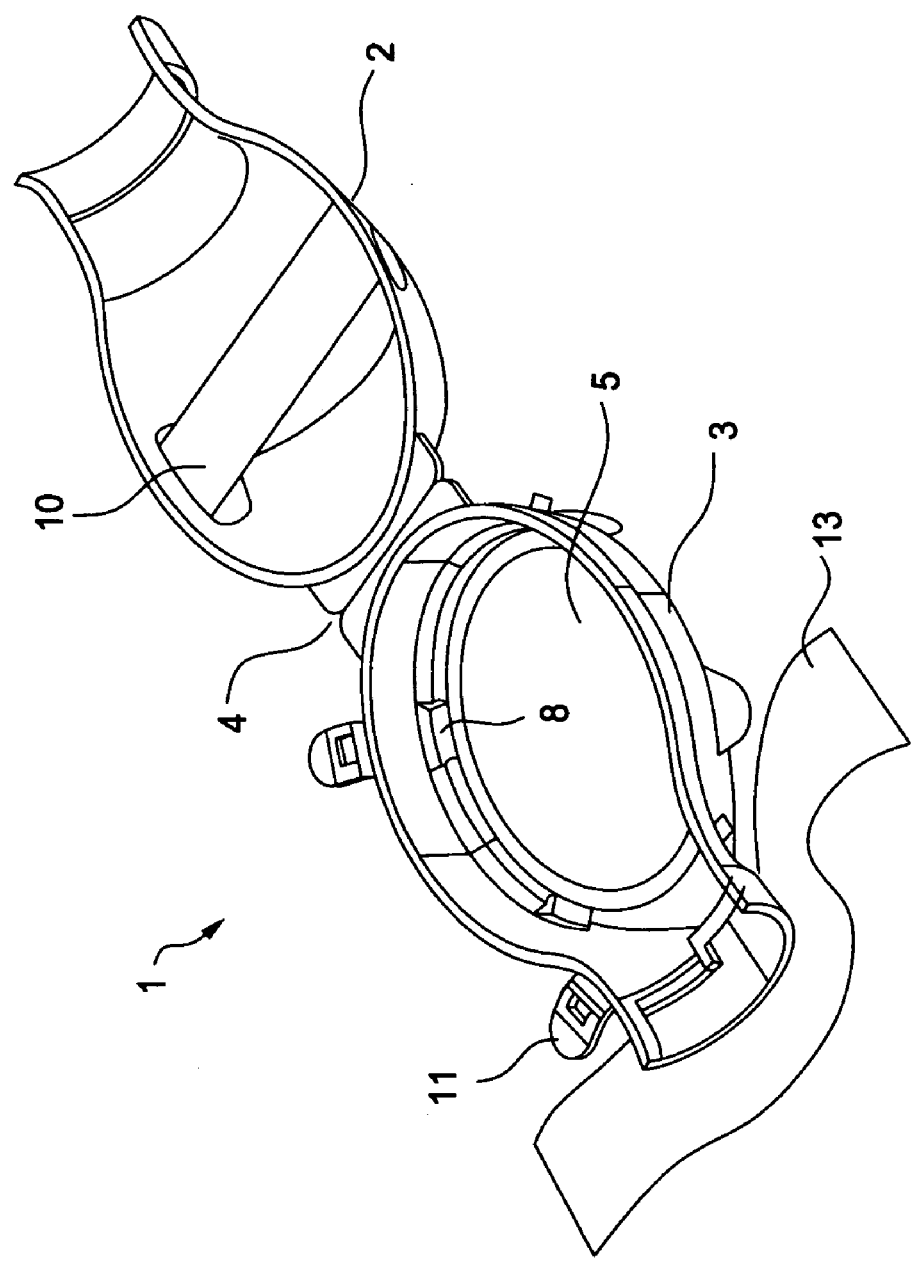
FIG. 5 is a perspective view of the negative pressure chamber shown in FIG. 1.
Figure 6:
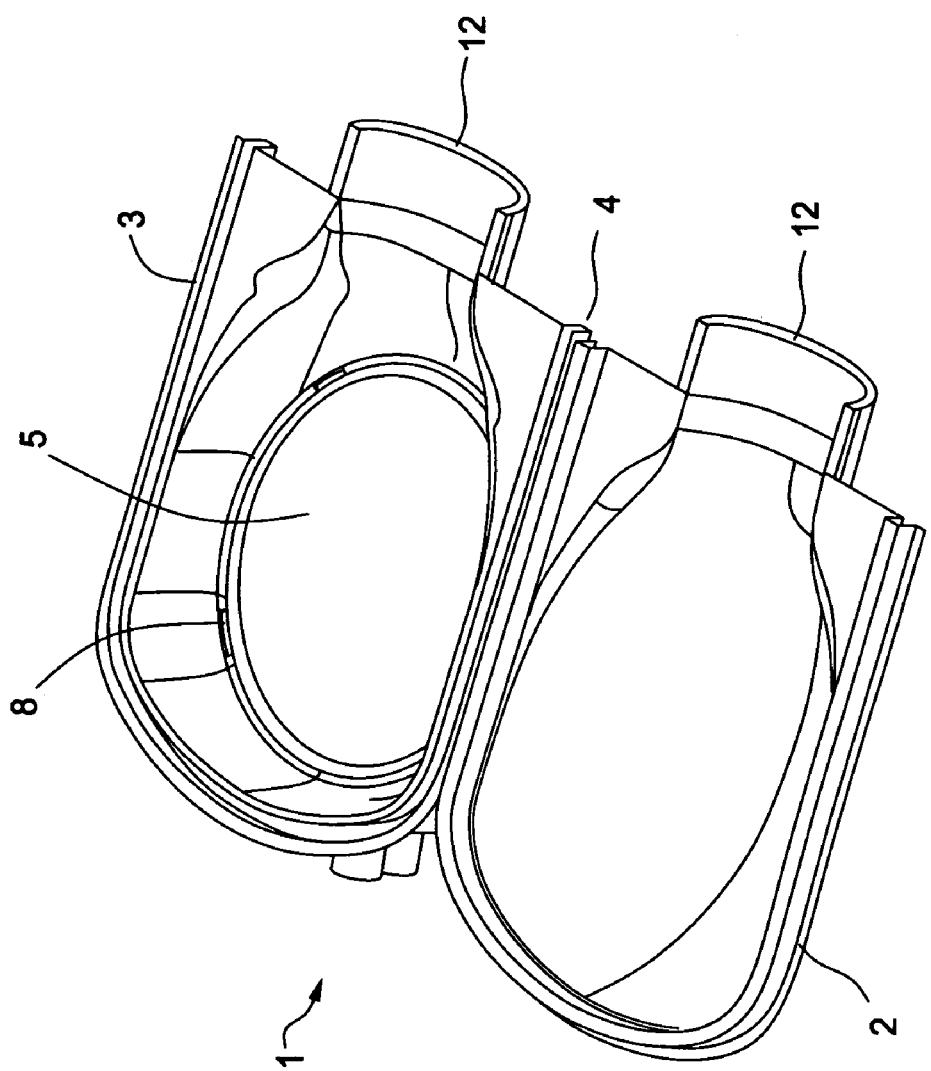
FIG. 6 is a perspective view of another embodiment of a negative pressure chamber.

FIG. 5 is a perspective view of the embodiment of a hand chamber shown in FIG. 1. The hand chamber (1) comprises an upper housing (2) and a lower housing.(3) that may be joined at either the front of the chamber, as shown in FIG. 5, or at the side of the chamber, as shown in FIG. 6, by a hinge (4) for the convenience of the user. In other embodiments, such as the embodiment described with respect to FIGS. 7 and 8, an upper housing and lower housing of the hand chamber are joined by fasteners therebetween without an additional hinged attachment connecting the upper housing and lower housing. The chamber (1) may be transparent for convenient viewing of the appendage. The lower housing (3) of the chamber has an aperture (5) defined therein that is adapted to receive a heat exchange element (6), and through which a portion of the heat exchange element (6) including a hand contacting surface (7) of the heat exchange element (6) protrudes when mated. The bottom portion of the chamber contains recessed regions (8) or slots that accept fasteners (9), such as protruding regions, e.g., tabs, on the heat exchange element (6), as shown in FIG. 1, to secure the heat exchange element (6) to the chamber (1) in a reversible fashion such that the heat exchange element and the chamber can be disassembled from each other and re-assembled together. The chamber (1) may be attached to the heat exchange element (6) using less than about 5 pounds of force so that it is easy to both attach and remove the heat exchange element (6). The gap between the heat exchange element (6) and the chamber (1) is typically minimized once a vacuum is applied because the vacuum force pulls the, two parts closer together. For instance, if the heat exchange element (6) is 5 inches by 7 inches and the negative pressure is approximately 1 psi, then the clamping pressure created by the negative pressure is approximately 35 psi.

The upper housing (2) of the chamber may include a strap (10) to secure a hand on the heat exchange element when the chamber is closed to ensure adequate contact for efficient thermal conduction. However, the force applied by the strap on the hand should not be so great as to restrict blood flow. The heat exchange element (6) mates to the lower housing (3) of the chamber (1) to form a leak resistant seal between the heat exchange element (6) and the lower housing (3) of the chamber (1). Sealing mechanisms between the heat exchange element (6) and the chamber (1) will be further described below.

Figure 7:
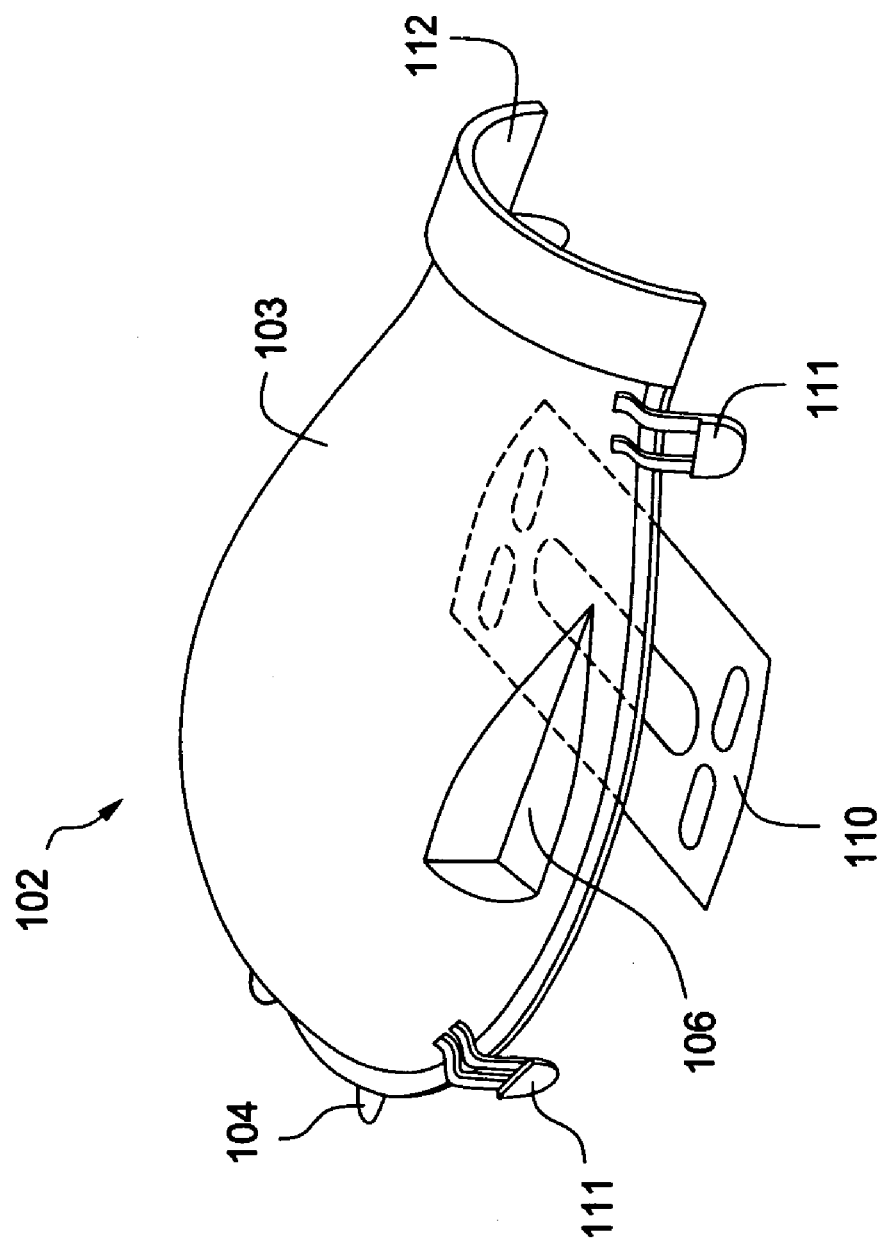
FIG. 7 is a perspective view of an upper portion of another embodiment of a negative pressure chamber.

FIGS. 7 and 8 illustrate another embodiment of a hand chamber. An upper housing (102) of a hand chamber is shown in FIG. 7. Upper housing (102) includes upper body portion (103) and an upper portion (112) of a hand opening. Tab (104) is located on an upper portion (112) to provide alignment between an upper housing (102) and a lower housing (120) of a hand chamber (shown in FIG. 8). Fasteners (111), such as tongs, on the perimeter of the upper body portion (103) engage with slots (124) in a lower body portion (122) of the lower housing (120) of the chamber to secure the upper and lower body portions to one another. The upper body portion (103) may have recesses (106) disposed in the dome portion to facilitate placement and removal of the upper portion. Strap (110) is attached to the perimeter of the upper body portion (103) and is adapted to hold a hand disposed in the hand chamber on the heat exchange element to prevent the force of vacuum pressure in the chamber from forcing a hand off the heat exchange element.

FIG. 8 shows the lower body portion (122) of the lower housing (120) of the chamber including a lower portion (108) of a hand opening. The lower housing (120) of the chamber also defines an aperture (105) therein, wherein the aperture (105) is sized to accommodate a portion of a heat exchange element disposed therethrough. Optionally, the lower body portion (122) comprises a tab (126) to align the upper housing (102) and the lower housing (120) of the hand chamber.

The lower body portion (122) comprises one or more recessed regions (118) that mate with one or more protruding regions or tabs of a heat exchange element in a reversible manner such that the chamber and the heat exchange element can be disassembled from each other, as described above with respect to FIG. 2.

The lower portion (108) of the hand opening may include fasteners (136) that attach the hand seal (113) to the lower portion (120) of the chamber through apertures (139) in the hand seal (113). Alternatively or additionally, the hand seal is attached to the chamber using an adhesive as described below. The hand seal (113) comprises a middle region (117) and end regions (116), (114). Middle region (117) is attached to the hand chamber, while end regions (116), (114) are free, i.e., not attached to the hand chamber. Attaching the middle of the hand seal to the hand chamber rather than an end region (116), (114) helps prevent over-tensioning of the seal that may occur with a seal that is attached to the chamber at the end of the seal.

Gasket (128) provides a seal between the lower housing (120) of the hand chamber and the upper housing (102) of the hand chamber. The gasket is positioned in a groove in the lower housing and/or in the upper housing of the appendage chamber. Gasket (134) provides a seal between the lower housing (120) of the hand chamber and a heat exchange element.

A heat exchange element cover (130) may be located between the gasket (134) and the lower body portion (122). The heat exchange element cover (130) may be heat sealed to the lower body portion (122) such that it can be removed and replaced after each use. Heat exchange element cover (130) comprises apertures (132) that allow vacuum ports to be disposed therethrough. A disposable vacuum port cover (138), such as a piece of filter paper sized to cover the apertures (132) may be provided in the chamber to protect vacuum ports disposed through the apertures from contamination from a hand in the chamber.

In one embodiment, the heat exchange element cover comprises a double-sided adhesive material. A first side of the double-sided adhesive material provides an adhesive surface to attach the heat exchange element cover to a heat exchange element. A second side of the double-sided adhesive material provides an adhesive surface that seals a hand positioned thereon to the heat exchange element cover, and thus, to the heat exchange element. The double-sided adhesive material is thermally conductive to allow heat emitted from the heat exchange element to be transmitted therethrough to a hand positioned on the heat exchange element cover.

Figure 9A:
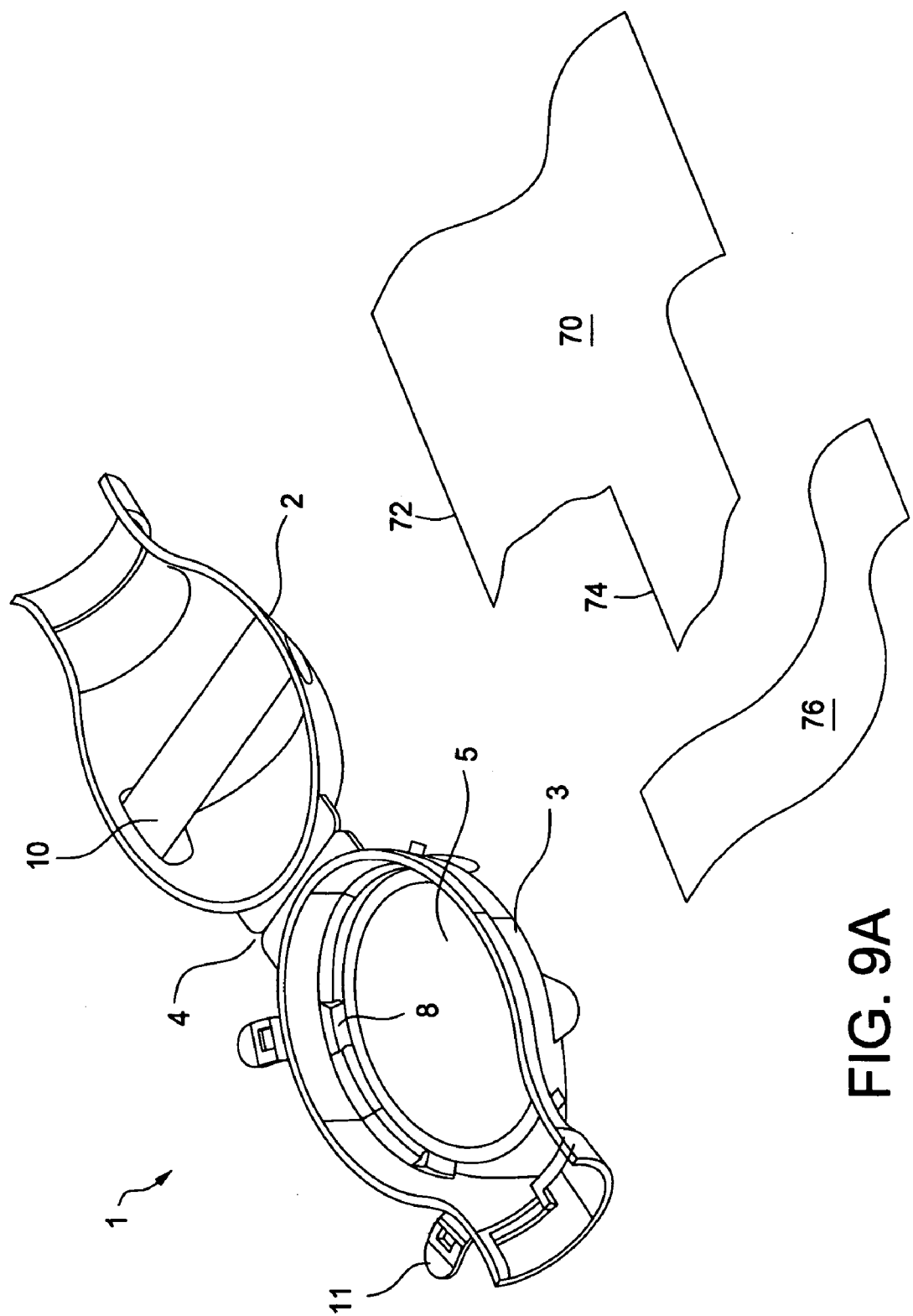
FIG. 9A is a perspective view of another embodiment of a negative pressure chamber and a hand seal.

FIG. 9A illustrates an embodiment of a heat exchange element cover (70) comprising a double-sided adhesive material. For use with the chamber (1), the heat exchange element cover (70) is placed over the opening (5) in the chamber (1) such that it contacts a heat exchange element that protrudes through the opening. The heat exchange element cover (70) may be a disposable component that prevents or minimizes patient contact with the heat exchange element and chamber, both of which may be reusable. The heat exchange element cover (70) comprises a first region (72) that is adapted to adhere to a heat exchange element on a first side of the first region (72) and is adapted to adhere to a hand positioned thereon on a second side of the first region (72). In addition to adhering to the palm side of a hand positioned thereon, the first region (72) may be wrapped around all or a portion of the backside, i.e., dorsal side, of the hand, depending on the size of the hand. The heat exchange element cover (70) also comprises a second region (74) that is adjacent to the first region (72) and is adapted to fit within the hand chamber (1) between a heat exchange element disposed in the chamber and the hand opening of the chamber. Second region (74) may comprise a double-sided adhesive material, a single-sided adhesive material, or no adhesive material. Preferably, the second region (74) comprises an adhesive material and is of a size such that the second region (74) may be wrapped around the portion of a wrist immediately adjacent a hand in the chamber such that the wrist does not directly contact the chamber. Hand seal (76) is provided as a separate piece that wraps around all of a portion of the wrist opening of the hand chamber and may also be disposable.

Figure 9B:
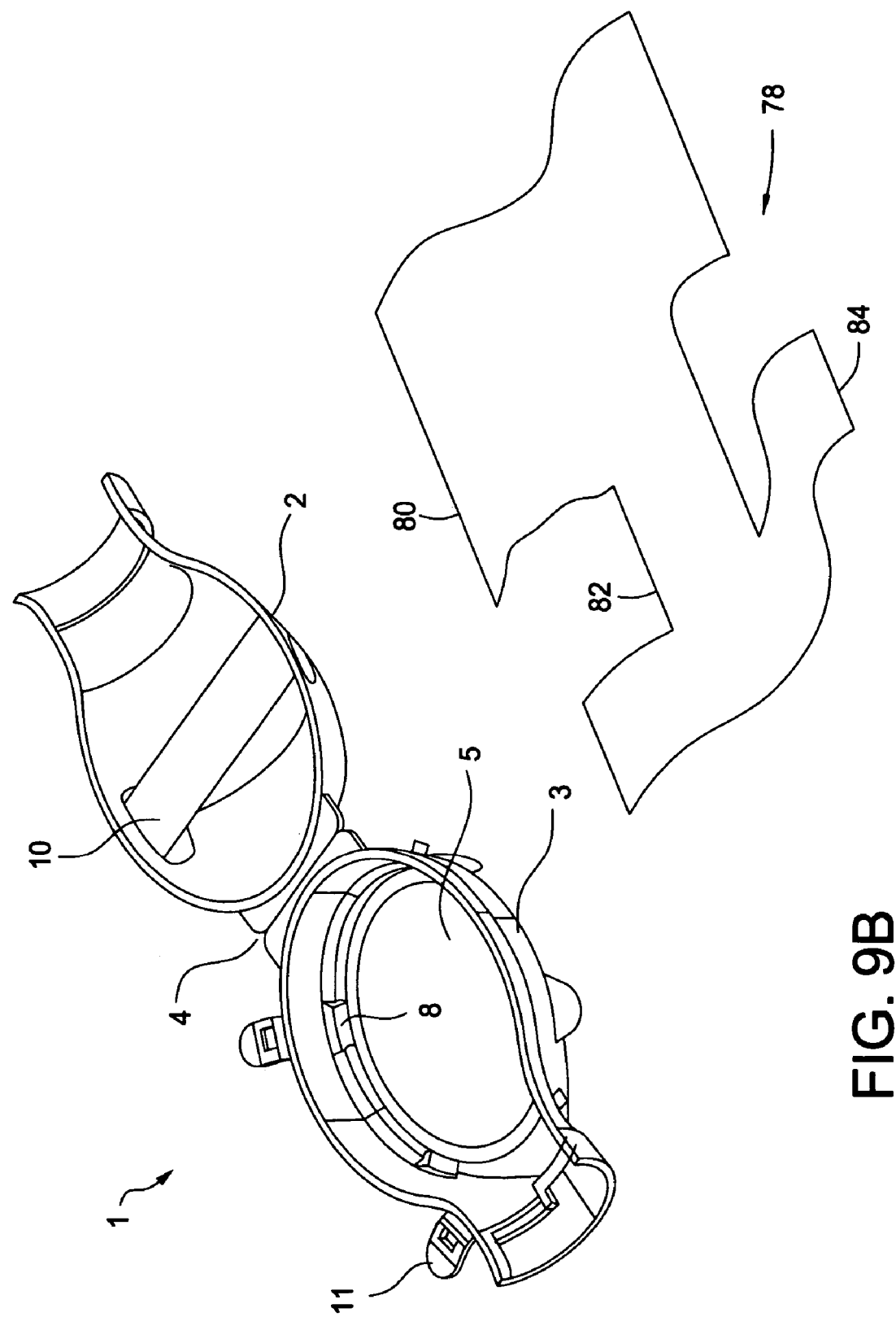
FIG. 9B is a perspective view of the negative pressure chamber of FIG. 9A and another embodiment of a hand seal.

In a further embodiment, the heat exchange element cover and the hand seal may be provided as one piece. The one piece heat exchange element cover and hand seal may be disposable. FIG. 9B illustrates an embodiment of a one piece heat exchange element cover and hand seal (78) comprising a double-sided adhesive material. The one piece heat exchange cover and hand seal (78) may comprise a double-sided adhesive material over its entire surface. Alternatively, the one piece heat exchange cover and hand seal (78) may comprise a double-sided adhesive material in a first region (80) of the one piece heat exchange element cover and hand seal adapted to adhere to the heat exchange element, a singled-sided adhesive material in a second region (84) of the one piece heat exchange element cover and hand seal adapted to adhere the chamber to the wrist, and a double-sided adhesive material, single-sided adhesive material, or no adhesive material in a third region (82) of the one piece heat exchange element cover and hand seal between the first and second regions. For use with the chamber (1), the first region (80) is placed over the opening (5) in the chamber (1) such that it contacts a heat exchange element that protrudes through the opening. The first region (80) may be wrapped around all or a portion of the backside of a hand positioned thereon. Preferably, the third region (82) comprises an adhesive material and is of a size such that the third region (82) may be wrapped around the portion of a wrist immediately adjacent a hand in the chamber such that the wrist does not directly contact the chamber. Further aspects of hand seals and adhesive materials that may be used therewith are provided below.

Figure 10A:
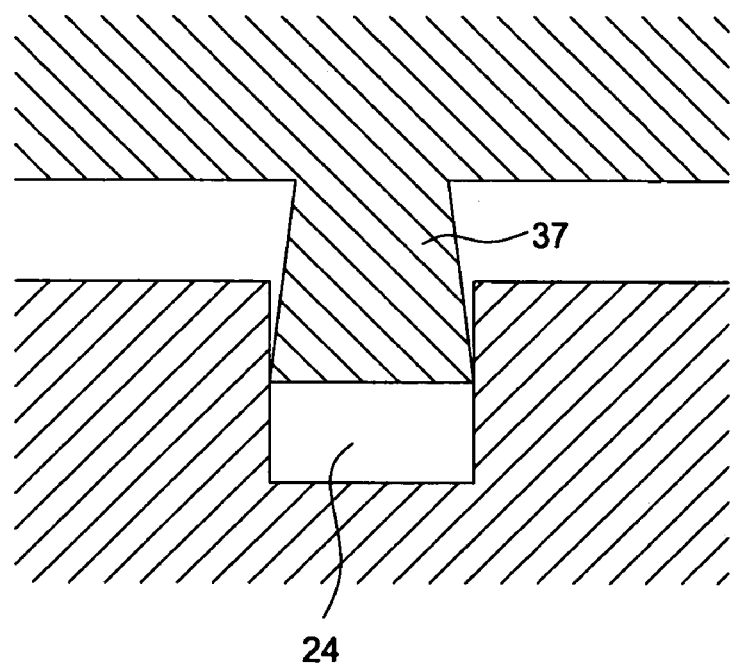
FIG. 10A is a schematic view of a seal between portions of the negative pressure chamber or between the negative pressure chamber and the heat exchange element in another embodiment of the invention.
Figure 10B:
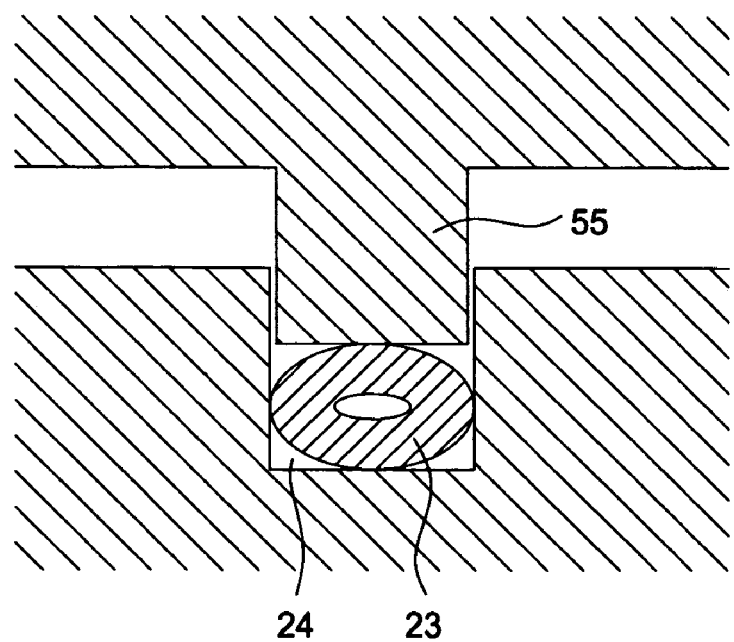
FIG. 10B is a schematic view of another seal between portions of the negative pressure chamber or between the negative pressure chamber and the heat exchange element in another embodiment of the invention.

FIGS. 10A and 10B illustrate embodiments of seals between the lower housing of the hand chamber and the heat exchange element and of seals between the upper and lower housings of the chamber. The seal between the lower housing of the hand chamber and the heat exchange element may include an interference tongue and groove type fit. The interference tongue (37) may be chamfered to ensure a tight fit with the groove (24), as shown in FIG. 10A. The seal between the top and bottom portions of the chamber may comprise an elastomer gasket (23) or alternatively, an elastomer gasket (23) in the bottom of a groove (24) with a tongue (55) as shown in FIG. 10B. The elastomer gasket (23) may be used as the gasket (128) between the lower housing of the chamber and the upper housing of the chamber and/or as the gasket (134) between the lower housing of the chamber and a heat exchange element, as discussed above with respect to FIG. 8. The groove can be in either the upper portion (2) or the lower portion (3) of the chamber (1). The gasket (23) may line the entire groove (24), and may be about ⅛ inch thick, for example. The gasket (23) may have a hollow center to further improve its compliance.

Fasteners are used in addition to a seal to join the upper and lower housings of the hand chamber. The fasteners preferably hold the mating surfaces of the upper housing and the lower housing of the chamber together until the vacuum is applied. Once vacuum is applied, the upper and lower housings as well as the heat exchanger are held in sealed abutment with each other. An exemplary appendage chamber (such as for the hand) has a top and bottom surface area of about 150 square inches or greater, e.g., approximately 5 inches by 10 inches, with a negative pressure of approximately 1 pound per square inch (psi), so there will be approximately 150 lbs of pressure forcing the upper and lower housing together, as long as the vacuum capacity is high enough to overcome the initial leakage. Preferably, a vacuum pump having a pump flow rate of at least 4 liters per minute, and more preferably 12 liters per minute or more, is used.

Figure 11A:
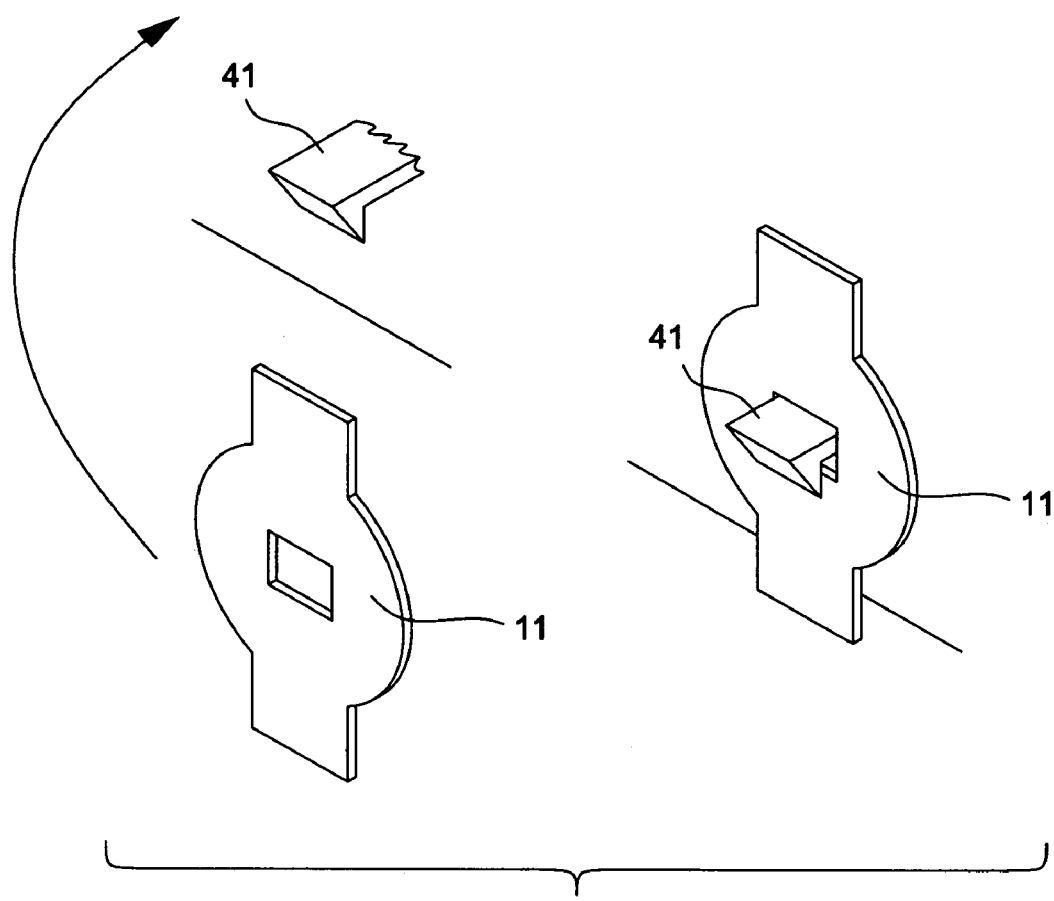
FIG. 11A is a schematic of an embodiment of a fastener to secure the upper housing of a negative pressure chamber to the lower housing of the negative pressure chamber.

Any type of fastener may be used to join the upper and lower housings of the hand chamber. For example, fasteners such as snaps, tabs, tongs, adhesives, or Velcro may be used. As shown in FIG. 1, in one embodiment, snap clips (11) may be positioned on either side of the appendage opening (12), and around the outer edge of the chamber (1). The snap clips (11) are preferably molded into the chamber (1) and made of the same material as the chamber for manufacturing efficiency. The snap clips can be molded into the lower housing and fastened by flipping them up from the lower housing to the upper housing and engaging tabs (41) molded into the upper housing, as shown in FIG. 11A. Alternatively, the snap clips can be molded into the upper housing and fastened by flipping them down from the upper housing to the lower housing and engaging tabs molded into the lower housing. The snap clips (11) may be designed to be single use fasteners such that the clips break when opened or reused, preventing repeated use of a disposable embodiment of the chamber.

Figure 11B:
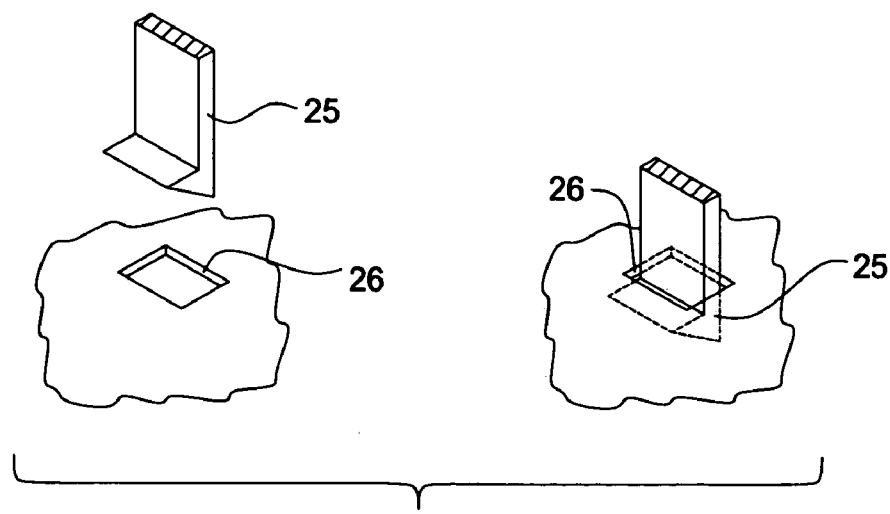
FIG. 11B is schematic of another embodiment of a fastener to secure the upper housing of a negative pressure chamber to the lower housing of the negative pressure chamber.

FIG. 11B shows a tong (25) that may be used as a fastener to join the upper and lower housing of the hand chamber. The tong (25) is preferably molded into the upper housing (2) and indexes with a slot (26) in the lower housing (3) when the chamber (1) is closed.

In any of the embodiments described herein, the upper housing of the chamber may further comprise an inner lining (not shown) to facilitate the comfort of the patient. As the hand is heated and negative pressure is applied, the hand surface not in contact with the heat exchange element may begin to perspire. The inner lining may comprise a breathable and/or moisture-wicking material. Examples of materials that may be used in the inner lining include polypropylene and synthetic, moisture-wicking fabrics used in exercise clothing.

The hand chamber can be made of a material such as a stainless steel, titanium, glass, aluminum, an acrylic material, polystyrene, high density polyethylene (HDPE), low density polyethylene (LDPE), poly(vinyl chloride), polypropylene, etc., or any biocompatible, disposable material. In disposable embodiments, the chambers are made of low cost materials. Disposable liners or inserts may be used with non-disposable chambers to meet health and safety requirements. Preferably, the chamber is a disposable acrylic chamber that allows viewing of a hand positioned in the chamber. The chamber may also be made of materials that may be sterilized via autoclaving or ethylene oxide sterilization. This is especially important if the apparatus is used during surgery where sterile conditions are very important. Disposable chambers and liners may be manufactured and packaged such that they are sterile before use.

While the hand chambers shown herein comprise an upper housing and a lower housing, one piece hand chambers may also be used. However, the chambers shown and described herein that include an upper and lower housing and the hand seals described herein provide easier access for inserting a hand into the chamber than, for example, a one piece chamber having an elastic seal. A hand of an unconscious patient may be easily inserted into embodiments of the apparatus of the invention, as the hand may be easily placed in a lower housing of the chamber. The upper housing of the chamber may then be aligned and attached to the lower housing of the chamber. Thus, it is not necessary to insert the patient's hand through a narrow hand opening of the chamber as is required with a one piece chamber that does not disassemble into an upper and lower housing.

Although in a preferred embodiment of the invention, the hand chamber is not permanently attached to the heat exchange element, one or more parts of the chamber may be permanently attached to the heat exchange element in alternative embodiments. For example, the lower housing of the chamber may be permanently attached to the heat exchange element while the upper housing of the chamber is disposable. Alternatively, the upper housing of the chamber may be permanently attached to the heat exchange element while the lower housing of the chamber is disposable.

Good contact with the heat exchange element is important in maximizing heat transfer to the hand. However, the pressure differential from ambient pressure to the interior of the chamber may cause the hand to be pulled into the hand opening. This pressure differential may cause the hand to ride up over the heat exchange surface of the heat exchange element and lose optimal contact for efficient heat exchange. The force caused by the pressure differential is approximately equal to the area of the hand or hand opening times the pressure differential. In one embodiment, the pressure differential is approximately three pounds. In addition, the hand may be forced off the heat exchange element through normal jostling or positioning of the patient. In one embodiment, the chamber may be oriented on its side if the patient's arm is strapped to the patient's body. In such an embodiment, the natural tendency will be for the hand to move off the heat exchange surface and compromise heat transfer between the hand and the heating surface. Accordingly, the following embodiments reduce or prevent the hand from slipping off the heat exchange surface.

A mechanism to hold down the hand may reduce the tendency for the hand to ride up over the heat exchange surface, and to keep the hand in position during normal patient movement and positioning. In one embodiment, a hand can be held in position with an optional elastic strap (10) mounted to the inside of the upper portion of the chamber as shown in FIG. 5. The downward force on the skin on the back of the hand created by the strap (10) may be pre-calibrated such that it does not cut off blood flow in adjacent vasculature in a wide range of hand sizes. Loss of blood flow in the skin may be monitored by observing a white skin color at the strap interface with the hand. The downward force on the skin surface should ideally not exceed 40 mm Hg. Preferably, the position for the strap in an apparatus for a hand is over the knuckles, as shown in FIG. 12, since minimal blood flow is present through this area.

Figure 12:
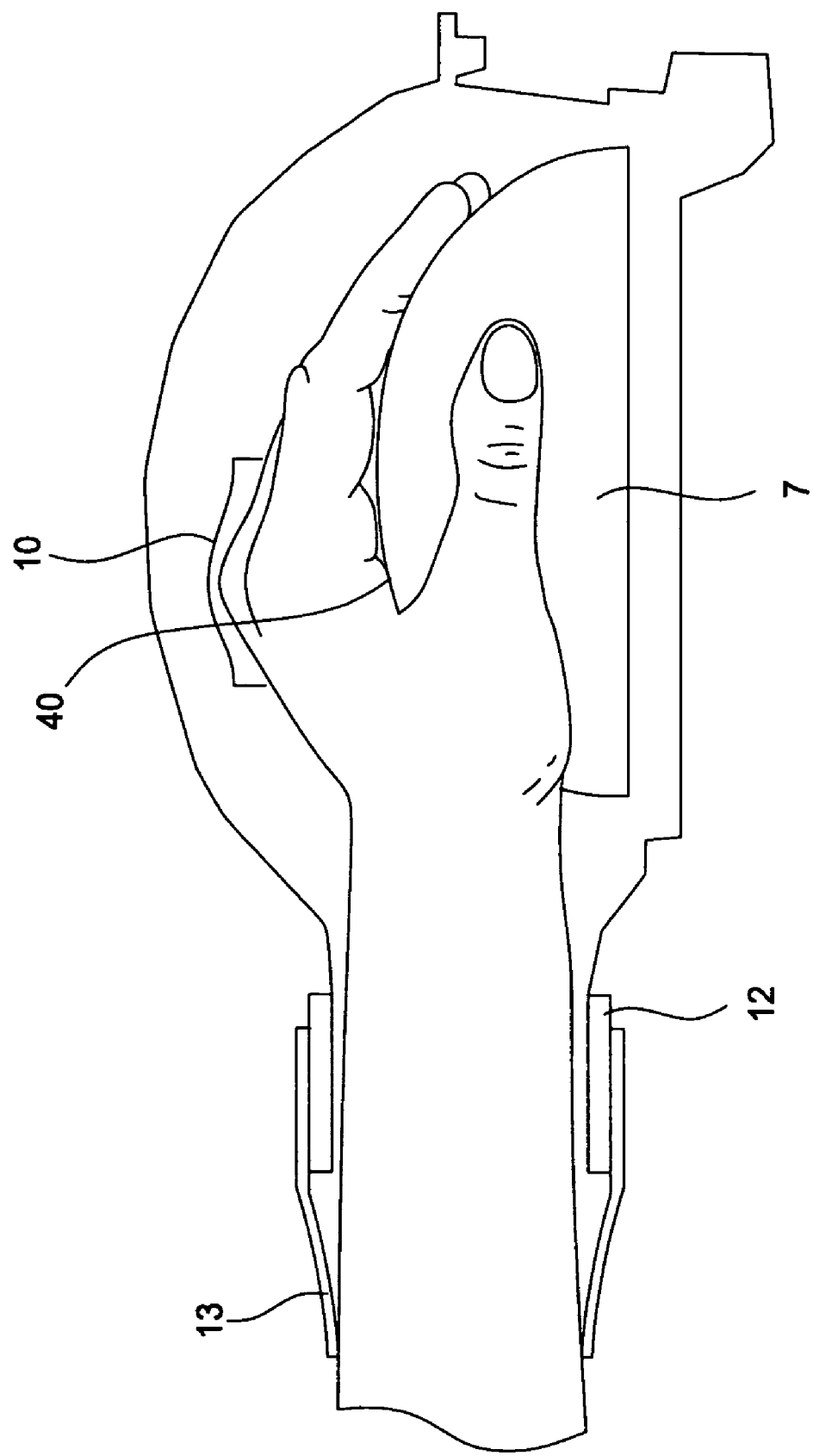
FIG. 12 is a side view of a negative pressure chamber having a hand disposed therein.

FIG. 12 shows a hand secured on a heat exchange surface (7) of a heat exchange element with a strap (10). In this embodiment, the hand contacting surface is dome shaped. The hand is preferably placed with the bottom of the palm low on the heat exchange surface (7) because the bottom of the hand opening is below the top of the heat exchange surface, such as about one inch below. In this configuration, the hand may be located horizontally such that the palm rests predominantly on the upslope (40) of the heat exchange surface. This upslope (40) prevents the hand from moving forward. In another embodiment, a post may be incorporated onto the heat exchange surface (7) between one or more fingers to prevent forward movement of the hand. The hand opening (12) of the chamber may be closely approximate the dimensions of the wrist.

In another embodiment, the heat exchange surface may be molded in the shape of a hand. For example, the heat exchange surface may have an imprint of an average human hand such that once the patient's hand is placed on top of the hand contacting surface, the patient's hand will be fixed in a single position. In yet another embodiment, the heat exchange surface may be tacky to prevent slippage of the hand from the hand contacting surface. For example, the heat exchange surface may be thinly covered with rubber or may be textured for enhanced grip. In other embodiments, the hand may be held down with adhesive on the heat exchange surface, or with a pliant, deformable material that is in place in the top portion of the chamber above the hand so that when the chamber is in the closed position, the hand is urged into contact with the heat exchange surface of the heat exchange element.

Figure 13:
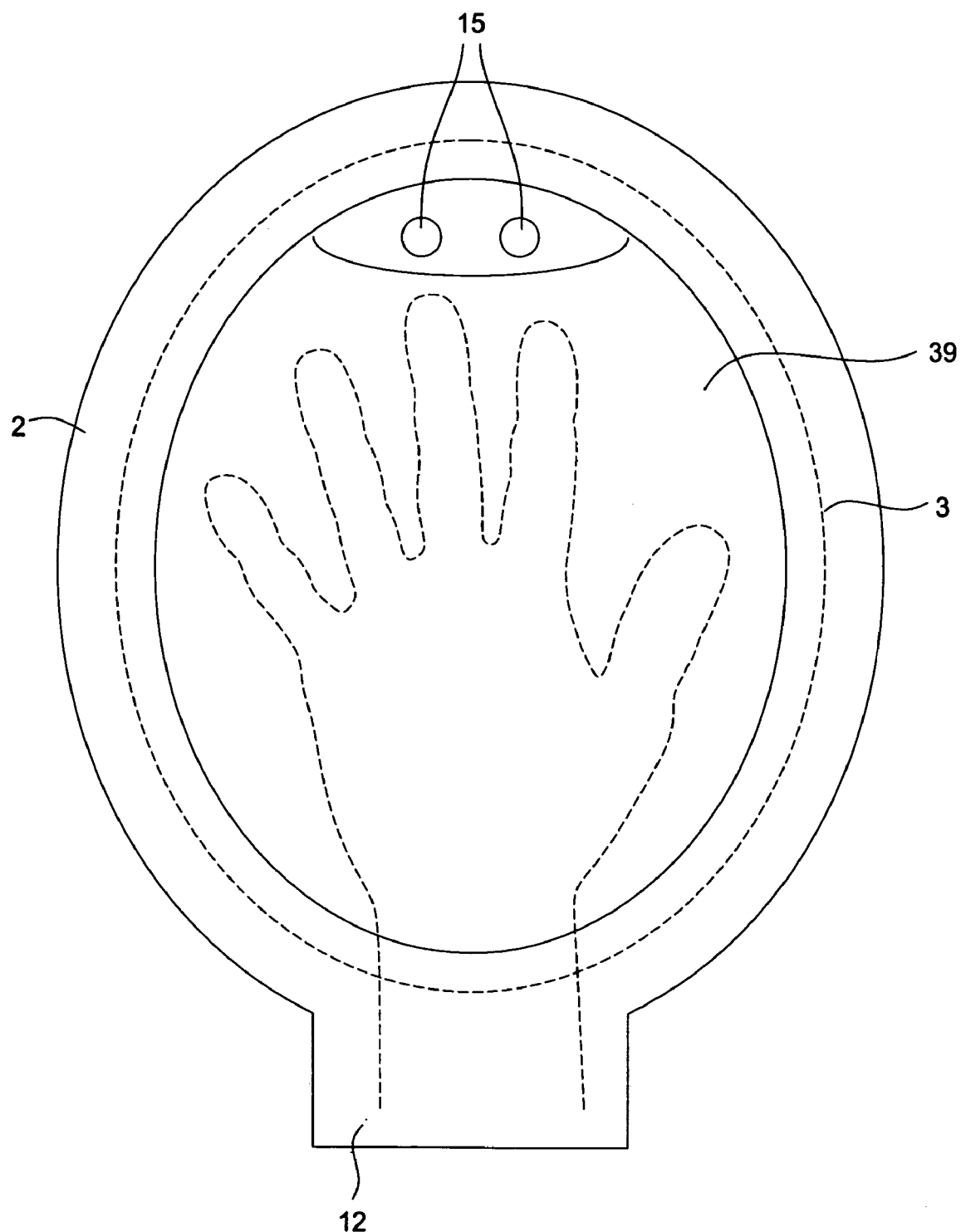
FIG. 13 is a top view of a negative pressure chamber having a hand disposed therein.

FIG. 13 shows a heat exchange element opening cover (39) that may be used to cover the heat exchange surface of the heat exchange element and the heat exchange element opening (5) (shown in FIG. 5) in the lower portion (3) of the chamber (1). The heat exchange element opening cover (39) may be elastomeric or a pre-formed, non-elastic material that deforms generally into the shape of the hand contacting surface when urged into contact with the heat exchange element. This material, if not heat conductive, is preferably less than 20 millimeters thick, to reduce the impact on heat exchange performance. In one embodiment, the heat exchange element opening is approximately 5 inches by 7 inches. The heat exchange element opening may additionally be covered by a rigid bottom cover (not shown) that is made from a metallic or plastic that is shaped to conform to a hand contacting surface of the heat exchange element. The heat exchange element opening cover provides a clean contacting surface for the hand placed thereon.

Once sealed to the hand, the chamber is still open to the outside air until the heat exchange element is attached, and the ultimate pressure seal is made between the lower portion (3) and the heat exchange element (6). The heat exchange element opening cover (39) preferably has openings or apertures to equalize the pressure between the heat exchange element and the hand chamber. Preferably, the apertures (15) are cut away portions of the heat exchange element opening cover (39) that would otherwise cover-vacuum ports to the chamber. The apertures prevent an elastic heat exchange element opening cover (39) from expanding or ballooning inside the chamber once vacuum is applied. Without such openings, such an expansion may force the hand off the heat exchange surface of the heat exchange element.

The hand seal that seals the hand to the hand chamber plays an important role in the performance of the apparatus because it prevents leakage of air into the vacuum chamber of the apparatus. As defined herein, the hand seal is a device used to prevent the leakage of air from the apparatus at the interface between the hand and the hand opening while the hand is enclosed within the apparatus. It is recognized that the hand seal is one example of an appendage seal that may be used with the appendage chambers of the invention. A hand seal with minimal leakage is preferable since it reduces the amount of air that must be continuously removed from the apparatus with an enclosed hand as vacuum is applied. However, a hand seal that exerts too much force on the hand may reduce or eliminate the return blood flow to the body, thus reducing the effectiveness of the device, and potentially creating adverse health effects such as are created with a tourniquet.

Figure 14:
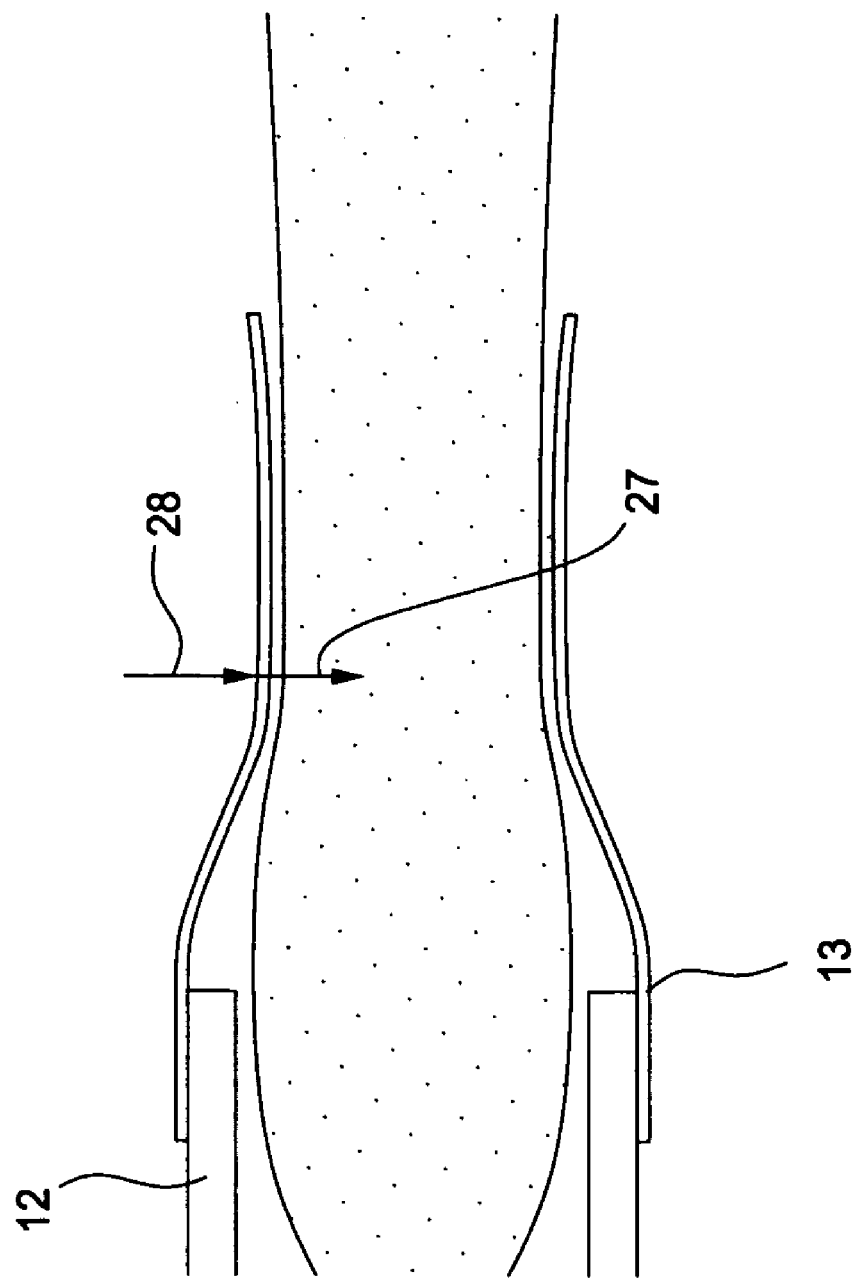
FIG. 14 is a cross-sectional view of an embodiment of a hand seal.

By way of explanation, two forces generally contribute to a tourniquet force on a hand surrounded by the hand seal. FIG. 14 shows an external hand seal (13) that is external to the hand opening (12) of the hand chamber. A hand in the hand chamber experiences the sealing force of the seal itself ($F_{seal}$) (27), which occurs in the absence of vacuum and a second force created by the atmospheric pressure forcing the seal against the hand, which is under negative pressure ($F_{vac}$) (28). A typical negative pressure is −40 mm Hg, i.e., 40 mm Hg below the ambient atmospheric pressure, which is very close to the pressure differential between systolic and diastolic pressures. $F_{seal}$ (27) and $F_{vac}$ (28) are additive and act in the same direction, as shown in FIG. 13. The sum of $F_{seal}$ (27) and $F_{vac}$ (28) equals $F_{total}$. When combined, $F_{seal}$ (27) and $F_{vac}$ (28) have the potential to create a tourniquet effect.

Although the effect differs from individual to individual, a tourniquet effect has been observed with a $F_{total}$ as low as 40 to 50 mm Hg. This tourniquet effect may be detected by observing a purple color in the hand as well as tingling and discomfort experienced by the patient.

The negative pressure applied by the $F_{vac}$ (28) is preferably maximized as much as possible without causing a tourniquet effect. The negative pressure causes the vasculature in a hand to dilate, promoting heat exchange with the body core. Therefore, if the seal is external to the hand opening (12), the $F_{seal}$ (27) should be minimized. A preferred external seal design has a $F_{seal}$ (27) less than about 20 mm Hg such that $F_{vac}$ (28) plus $F_{seal}$ (27) does not exceed 40 mm Hg.

Figure 15:
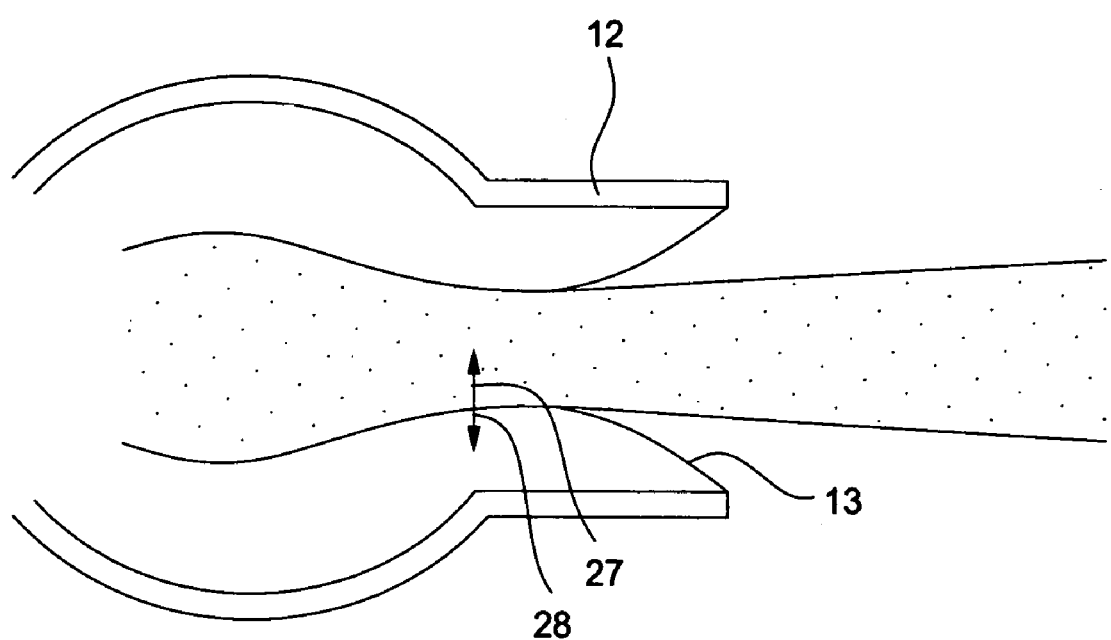
FIG. 15 is a cross-sectional view of another embodiment of a hand seal.

FIG. 15 shows a hand seal (13) that is internal to the hand opening (12). With an internal seal, the negative pressure applied by the vacuum pulls the seal away from the hand because $F_{seal}$ (27) and $F_{vac}$ (28) act in opposition to one another, thereby reducing the total force, $F_{total}$, and thus reducing the tourniquet effect. For example, a $F_{seal}$ (27) of 80 mm Hg and a high $F_{vac}$ can reduce the $F_{total}$ to 40 mm Hg.

Figure 16A:
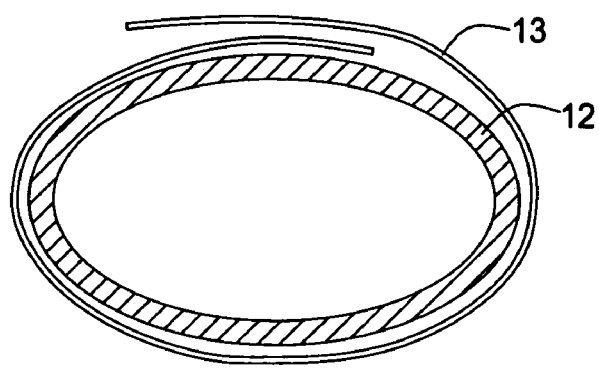
FIGS. 16A–16C are cross-sectional views of three other embodiments of hand seals.

In one embodiment, the hand seal (13) comprises a strip of releasable adhesive tape ranging in width from 0.5 inches to 6 inches in width. The seal (13) may have different widths along the length of the seal. The seal (13) may comprise an adhesive face and a backing. As shown in FIG. 16A, the seal (13) is generally long enough that when wrapped end over end around both the hand and the edge of the hand opening, an overlap of about 2 inches is present. The overlap is preferably not so great as to encourage the user to tightly wrap the seal (13) around the hand and thus create an unwanted sealing force greater than 20 mm Hg. The fixed dimension, i.e., non-elastic, enclosure of the hand opening of the chamber also reduces the tendency to overly tighten the seal (13).

Figure 16B:
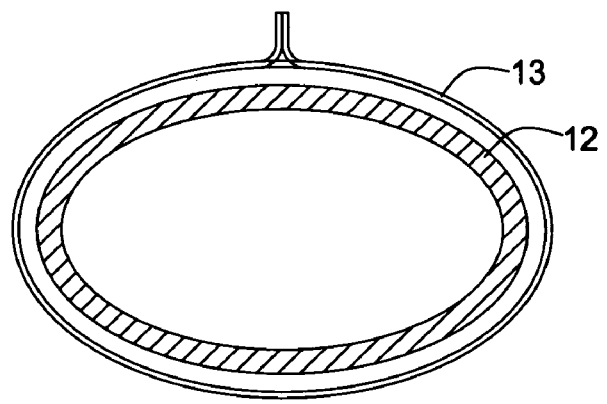

FIG. 16B shows an another embodiment of a hand seal (13) that is wrapped and held together such that the seal is pinched in on itself and the adhesive faces are stuck together.

Thus, the ultimate tension created on the hand is limited to the sticking force of the seal to itself because the seal peels away from itself to relieve the tension.

Figure 16C:
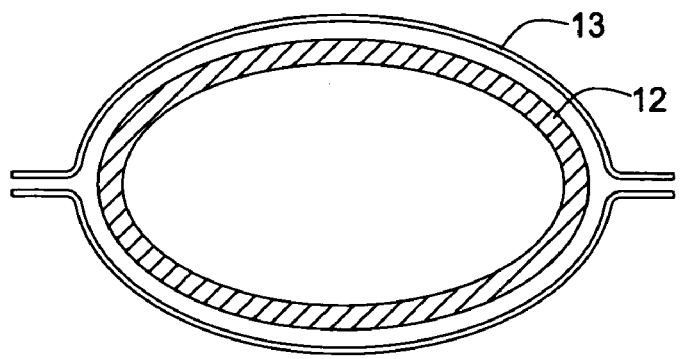

FIG. 16C shows an embodiment of a hand seal (13) comprising multiple pieces of sealing tape. Multiple pieces of sealing tape may be used with a hand opening (12) comprising multiple parts such that one or more parts of the hand opening have one or more pieces of sealing tape attached thereto.

In any of the hand seal embodiments described herein, the hand seal may be attached to one portion of the chamber for convenience, such as the upper or lower housing of the chamber. The seal may also be provided separately as a pre-cut strip or may be cut from a roll of seal material at the point of use. There may be a release liner on the adhesive face of the seal which is removed prior to use.

The hand seals provided herein typically comprise a releasable adhesive for attachment to a wrist. The hand seals may also comprise a more permanent adhesive to attach the seal to the hand chamber. The hand seals may also be attached to the chamber with fasteners in the chamber that are disposed through apertures in the seal, such as the fasteners (136) in the chamber and the apertures (139) shown in FIG. 8.

The releasable adhesive may be any of a wide variety of commercially available materials with high initial adhesion and a low adhesive removal force so that the seal does not pull off hair or skin and create pain when it is removed. It is also preferred that the adhesive be thick and malleable so that it can deform or give, in order to fill gaps. Adhesives with water suspended in a polymer gel i.e., a hydrogel, are generally effective. One example of such an adhesive is Tagaderm branded 3M adhesive (part No. 9841) which is a thin (5 mm) breathable adhesive that is typically used for covering burns and wounds. Another example is an electrocardiogram (EKG) adhesive such as 3M part No. MSX 5764, which is a thicker adhesive (25 mm). A thicker adhesive has better capabilities to fill gaps and conforms to fill wrinkles in the seal when the seal is applied. The seal should fasten such that the initial leakage of the apparatus is less than 6 liters per minute. Once a vacuum is applied, the pressure differential pulls the seal closer to the hand such that the seal around the hand is enhanced, and the leakage rate typically drops to less than 1 liter per minute.

In one aspect, the hand seal is a single use seal. For example, the releasable adhesive may be a single use adhesive. In one embodiment, the single use hand seal remains attached to the hand chamber after use, and the hand chamber and attached seal are disposed after a single use. In another embodiment, the hand seal may be removed from the chamber and the chamber may be used again with another hand seal.

The backing of the hand seal may be a thin, non-elastic, flexible material. The backing supports the adhesive and keeps it from being pulled under vacuum into the hand opening. The backing also allows the adhesive to conform to both the shape of the hand and the shape of the hand opening, as well as to fold in upon itself to fill gaps that may be present in the seal around the hand. Furthermore, the backing prevents the adhesive from sticking to other surfaces. Commercially available polyethylene in thicknesses up to about 10 millimeters may be used for the backing. Polyethylene that is thicker than about 10 millimeters may limit the adhesive's ability to fold upon itself and fill in gaps. The backing may also comprise any polymer that may be fabricated into a thin, non-elastic, flexible material.

In one embodiment, the hand seal comprises a backing surrounded by an adhesive such that the hand seal comprises two opposing adhesive faces. For example, 3M EKG adhesive product MSX 5764 contains a supportive backing in between multiple layers of adhesive. Multiple layers of backing can also be used to provide support for the seal.

Although an elastic backing may be used in the hand seal, an elastic support backing generally creates an inferior seal compared to a non-elastic support backing because the elastic support backing reduces the ability of the adhesive to fold against itself to fill gaps and to take up excess adhesive material. Also, the elastic backing creates a greater chance that the user will over tension the seal and thereby reduce blood flow.

The opening of the chamber is preferably close to the size of the patient's wrist to minimize the difference in dimensions that the hand seal must cover. The smallest opening size that will accommodate the hand size range is preferred. Minimizing the opening size reduces the force on the hand created by the pressure differential between the outside of the chamber and the inside of the chamber since the force caused by the pressure differential is approximately equal to the area of the hand or hand opening times the pressure differential. In one embodiment, the hand opening may be sized to receive a human wrist. The hand opening is preferably the same size as the 95th percentile wrist (about a 2" by 3" ellipse), such that the chamber may fit the majority of patients. The hand seal is typically able to accommodate wrist sizes down to the size of a small child using this opening size. Multiple opening sizes, such as small, medium, and large may be used to accommodate a wider range of wrist sizes.

Alternatively, the hand opening may be fabricated to contract within a size range without constricting blood flow in the hand to further minimize this force and make sealing easier. For example, one or more strings may be used to tighten the hand opening to a wrist. In another embodiment, external buckles and straps surrounding the hand opening may also be used to secure the hand opening around a hand.

In a further embodiment of the invention, the hand chamber may be collapsible for easy storage and for ease of transportation, such as to remote locations. The collapsible chamber may be disposable. The chamber may lay flat for storage and then expand or deploy to create a three dimensional chamber that resists collapse by negative pressure. FIGS. 17A–17C show examples of collapsible, disposable chambers. Generally, the collapsible, disposable chambers comprise a top portion (62), a bottom portion (63), a fastening means such as zipper (38), and a hand seal (64). The top portion (62) may be made from any flexible material including polymers such as nylons, polyesters, polystyrene, polypropylene, high density polyethylene (HDPE) or any other appropriate polymer. The flexibility of the top portion (62) allows the chambers to be folded for storage and expanded for use. The chamber may be strengthened by adding supports to the flexible top portion (62) to prevent it from collapsing against the appendage under negative pressure. Preferably, the top portion (62) of the chamber is transparent such that the condition of the appendage may be monitored during use of the apparatus.

The top portion (62) of the chamber may be sealed by a fastening means such as a zipper (38). However, the fastening means may be any mechanism which can secure the hand and form a vacuum tight seal. A hand seal (64) may be made with adhesive around the hand and the hand opening.

The bottom portion (63) of the chamber may be made from rigid plastic allowing it to engage and seal with the heat exchange element. The bottom-portion (63) preferably comprises a heat exchange element opening cover and mating holes (not shown) to engage the chamber with a heat exchange element. Heat exchange element surface (67) of a heat exchange element protrudes through an opening in the bottom portion of the chamber.

Figure 18:
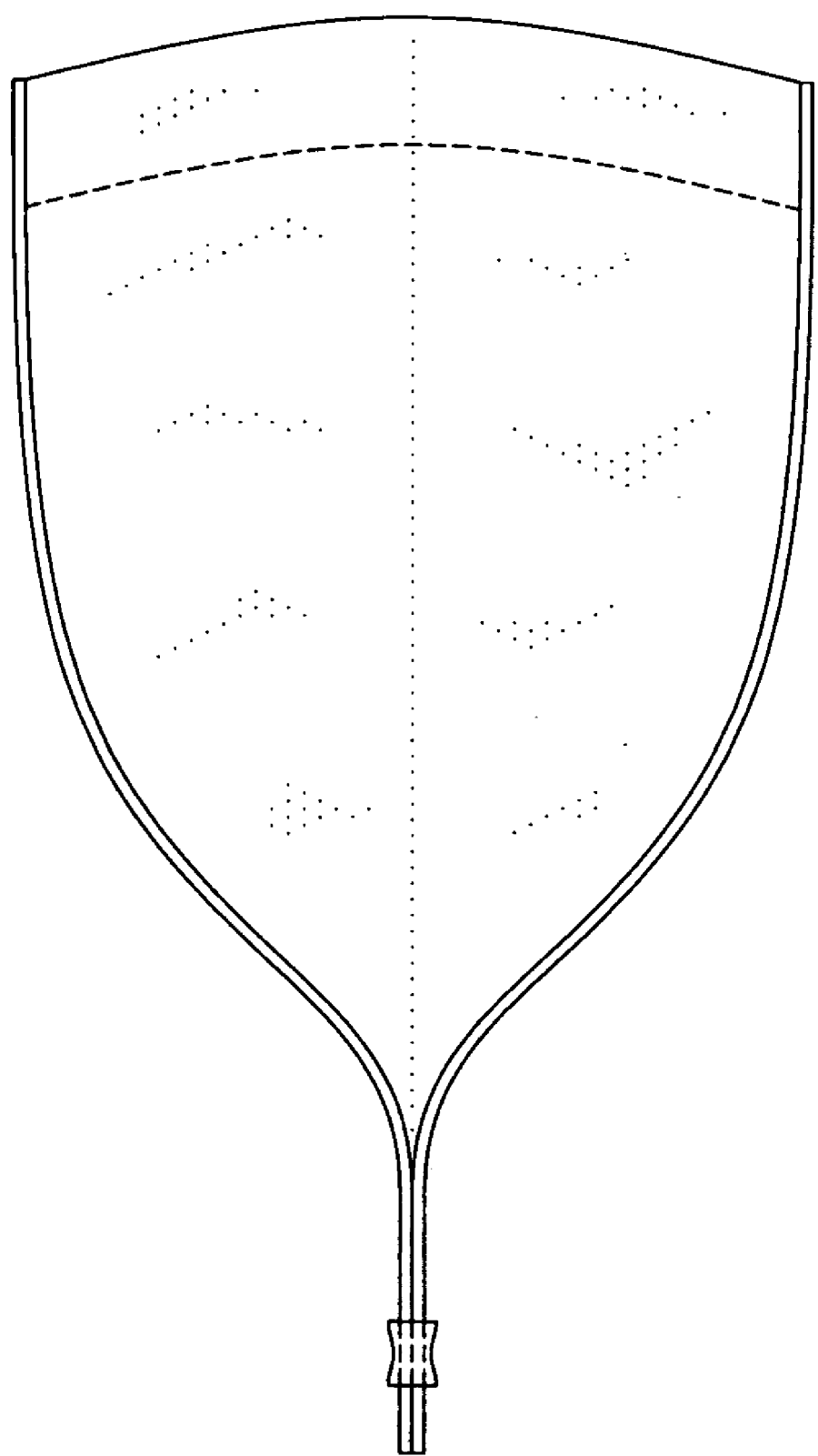
FIG. 18 is a perspective view of another embodiment of a storable apparatus of the invention.
Figure 19:
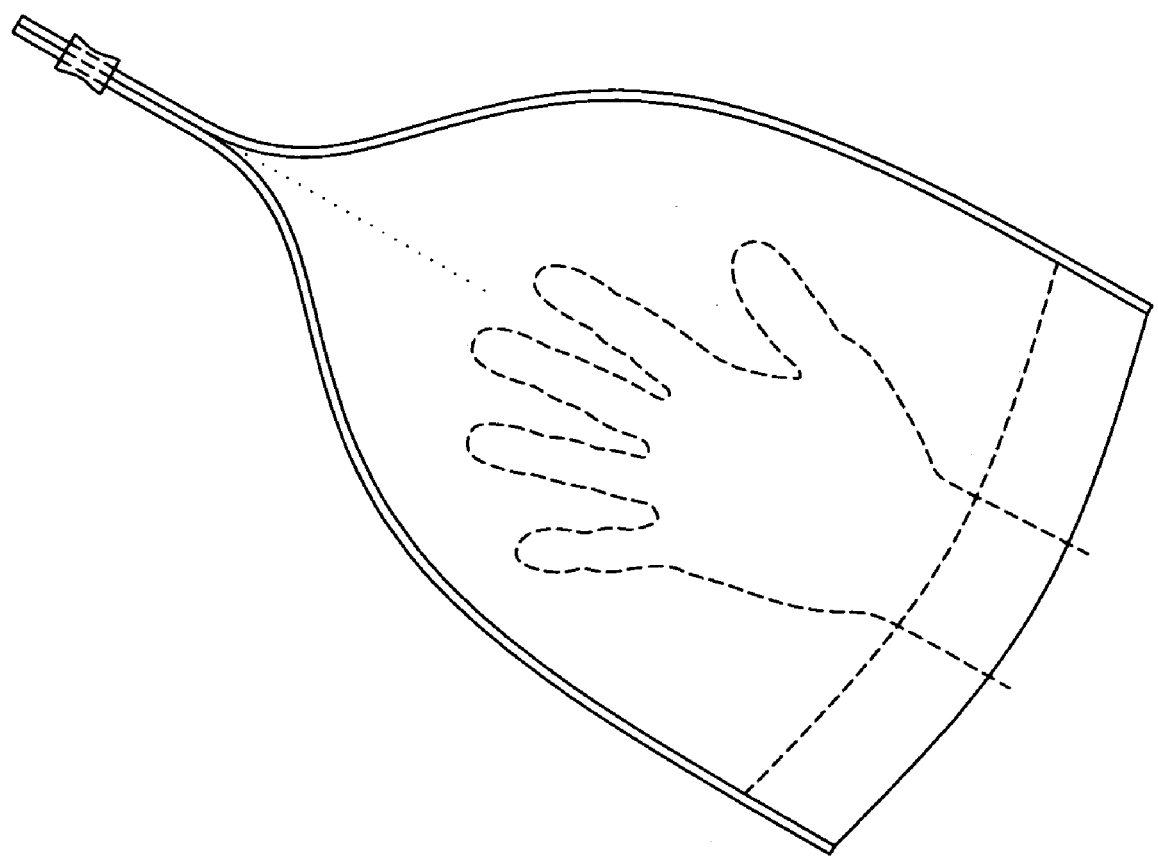
FIG. 19 is a perspective view of another storable apparatus of the invention with a hand disposed therein.
Figure 20:
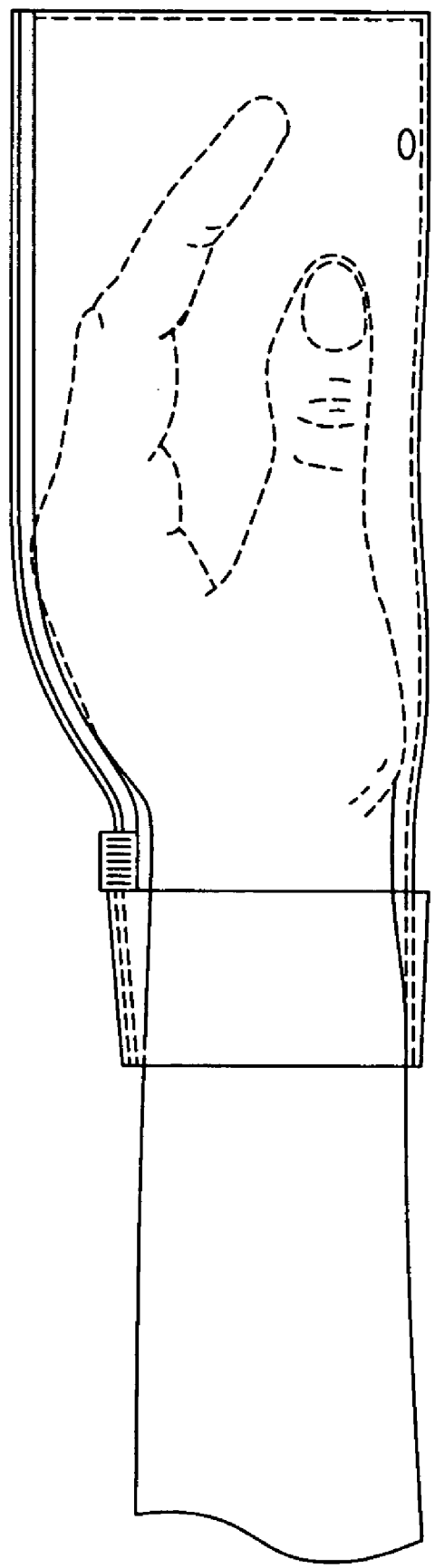
FIG. 20 is a perspective view of another storable apparatus of the invention with a hand disposed therein.

FIGS. 18–20 illustrate other embodiments of collapsible, disposable hand chambers. FIG. 18 shows an unsealed hand chamber that is substantially flat. FIG. 19 shows an unsealed hand chamber having a hand positioned therein. FIG. 20 shows a sealed hand chamber enclosing a hand therein. FIG. 20 shows that the substantially flat hand chamber of FIG. 18 can be expanded to receive a hand. The chambers in FIGS. 18–20 can be made from disposable plastic bags with zippers, such as food storage bags.

Figure 21:
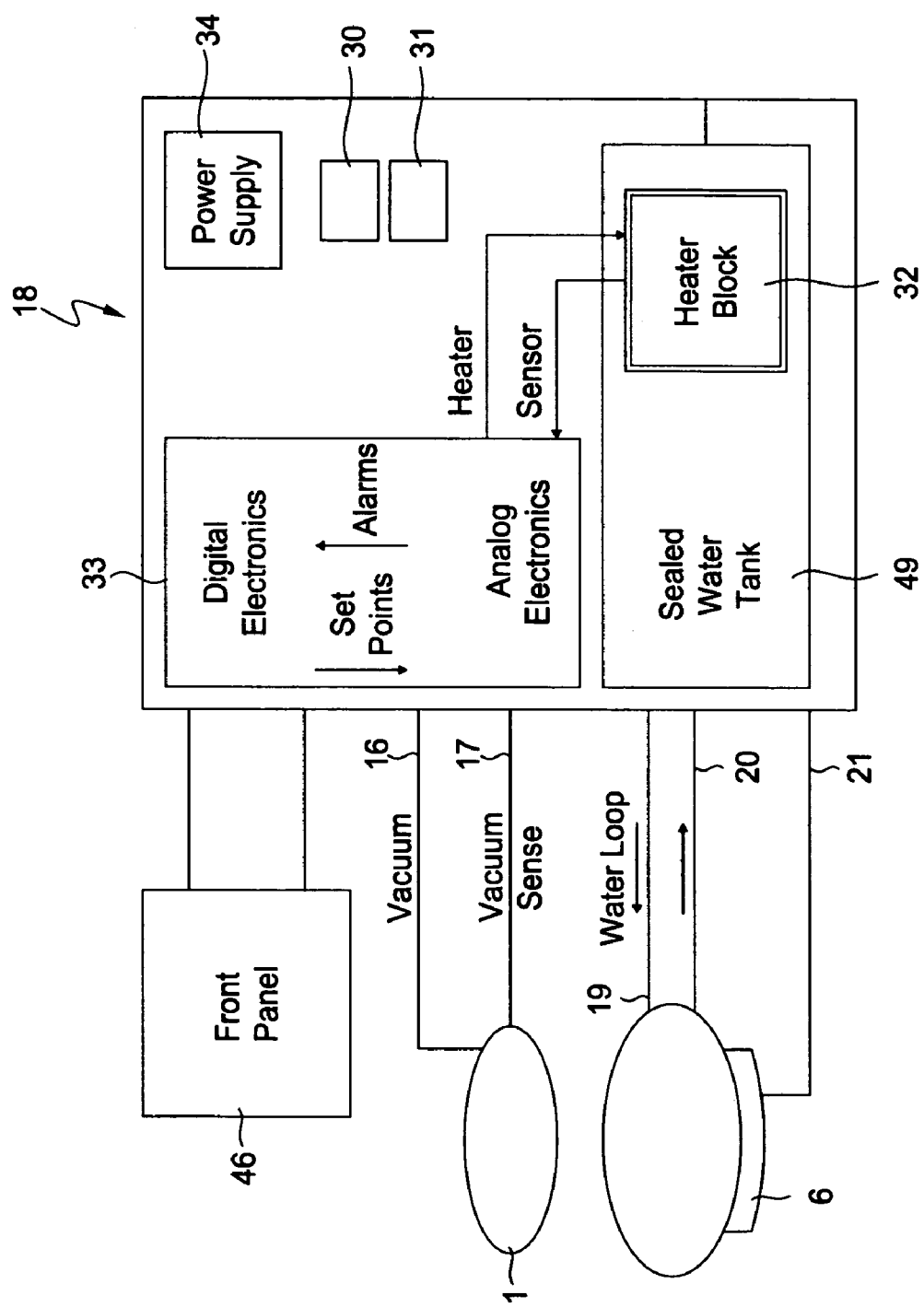
FIG. 21 is a schematic of an embodiment of a controller.

FIG. 21 shows an embodiment of a control unit for the hand chambers and heat exchange elements described therein. In one embodiment, a controller case houses all the electronics and mechanical devices required to control the temperature and the vacuum provided to the apparatus. The controller case (18) typically contains the following components: a vacuum pump (30), a heating medium pump (31), a heater (32), a heat exchange medium source (49), proportional-integral-derivative (PID) controllers for process control of the vacuum and the temperature (33), and a power supply (34). The control unit (18) settings are located on a front panel (46) that provides an operator interface. The control unit (18) may contain additional electronics for optimal operation of the apparatus. In alternative embodiments, the vacuum control and temperature control may be controlled by two different controllers.

The control unit (18) is preferably configured to minimize environmental noise, which may distract a surgeon during use of the device in an operating room. A magnetic drive pump may be used for the heating medium pump (31). Additionally, the negative pressure pump may be muffled. The pumps may be mounted on a frame which may be mounted inside a plastic case to further reduce the noise to about 60 decibels at 1 meter or more preferably below 55 decibels at 1 meter.

The controller (33) also preferably has safety features including a device shutdown feature that is activated if the apparatus sensors, such as the temperature and pressure sensors, fail or become disconnected. The controller may also include an alarm circuit that sounds a buzzer if the temperature of the apparatus is not regulated correctly. A relief valve may be provided within the vacuum loop of the apparatus such that the chamber may be vented if the vacuum within the chamber exceeds 100 mm Hg.

In one embodiment, the heater (32) comprises two cartridge heaters and a thermocouple mounted in a grounded aluminum block that is submerged in a water tank provided as the heat exchange medium source (49). The temperature at the hand in the hand chamber may be sensed with a thermocouple located in the hand chamber proximate the heat exchange surface of the heat exchange element positioned in the opening in the chamber. In one example, the heater is heated to a temperature of 46° C. to provide a temperature in the hand chamber of 43° C.

Vacuum may be applied to the apparatus by vacuum pump (30) connected to and located within the control unit (18). The vacuum pump (30) may be a diaphragm pump. The vacuum (16) and vacuum sense (17) lines are routed from the control unit (18) to the heat exchange element (6) in tubing. Once the lines reach the heat exchange element, they are routed to two vacuum ports (218), (220), which provide a port for a line that provides a vacuum therethrough and a port for a line that senses the vacuum conditions provided by the vacuum line, as shown and described with respect to FIG. 2. The vacuum ports are in open communication with the chamber through the heat exchange aperture in the lower portion of the chamber. The vacuum ports may be located in an area such as the front of the hand contacting surface away from the hand opening to avoid being blocked by the hand. However, the vacuum ports may be located anywhere in the heat exchange element as long as they are in open communication with the chamber. In another embodiment, vacuum generation and vacuum sensing is provided to the chamber by vacuum ports located inside the seal between the heat exchange element and the chamber.

A more accurate measurement of the vacuum provided in the chamber is obtained by locating the vacuum port that senses the vacuum conditions within the apparatus near the hand in the hand chamber, as shown in FIG. 2, rather than away from the hand chamber, such as within the control unit. For example, an amplified silicon pressure sensor may be used near the hand in the hand chamber.

The heat exchange element opening cover may be designed such that it does not interfere with the vacuum ports, as shown in FIG. 13. In an alternative embodiment, the heat exchange element automatically engages a fitting or a plurality of fittings on the chamber for the vacuum lines. When the heat exchange element is removed at the end of treatment, the fitting may be broken off, preventing reuse of the chamber. In one embodiment, the vacuum lines may be connected separately from the heating medium connections. An electronic vacuum monitoring device may also be mounted on the heat exchange element.

In a preferred embodiment, the heat exchange element (6) is connected to the control unit (18), as shown in FIG. 21. The connections include a heat exchange medium in line (19), a heat exchange medium out line (20), a vacuum line (16), a vacuum sense line (17) (or vacuum monitoring electronics), and temperature monitoring electronics (21). These lines may be bundled, contained, and strain relieved in a protective sheath (22) (shown in FIG. 3) that is connected to the control unit (18). The lines may also be contained in one extruded tube with different enclosures for each medium used, such as fluid, vacuum, and gas lines. In another embodiment, a vacuum sensing tube may be run from the heat exchange element (6) to the control unit (18) through a separate tube. In yet another embodiment, the vacuum line (16) and the vacuum sense line (17) may be contained in a separate sheath, independent of the heat exchange medium lines (19), (20). Preferably, the lines and sheathes are crush resistant.

In a preferred embodiment, the heat exchange element is coupled in a closed loop configuration with the source of the heat exchange medium. For example, the heat exchange element is coupled in a closed liquid loop configuration with a liquid tank housed within the control unit, which is the heat exchange medium source (49) shown in FIG. 21. The closed loop configuration reduces the maintenance requirements for the operator because it minimizes the loss of heat exchange medium that typically occurs if the heat exchange element is detached from the heat exchange medium source. Contamination of the heat exchange medium source is also minimized by the closed loop configuration. Contamination of the heat exchange medium such as water can also be reduced by adding an antimicrobial agent to the heat exchange medium source.

In an alternative embodiment, the heat exchange element and vacuum lines may be connected to the control unit using actuated fittings including quick release fittings with an automatic shut off mechanism. The automatic shut off mechanism halts the vacuum application and the heating medium flow as soon as the vacuum lines are disconnected. Actuated fittings may also allow the operator to change heat exchange elements. For example, the same control unit may be used for embodiments of the apparatus designed for different appendages.

An apparatus designed for treating a foot will be briefly described below. Generally, the apparatus designed for treating a foot may include the same components as the apparatus described above for treating a hand. Typically, the apparatus for treating a foot also functions in a similar fashion to the apparatus for treating a hand.

Figure 22:
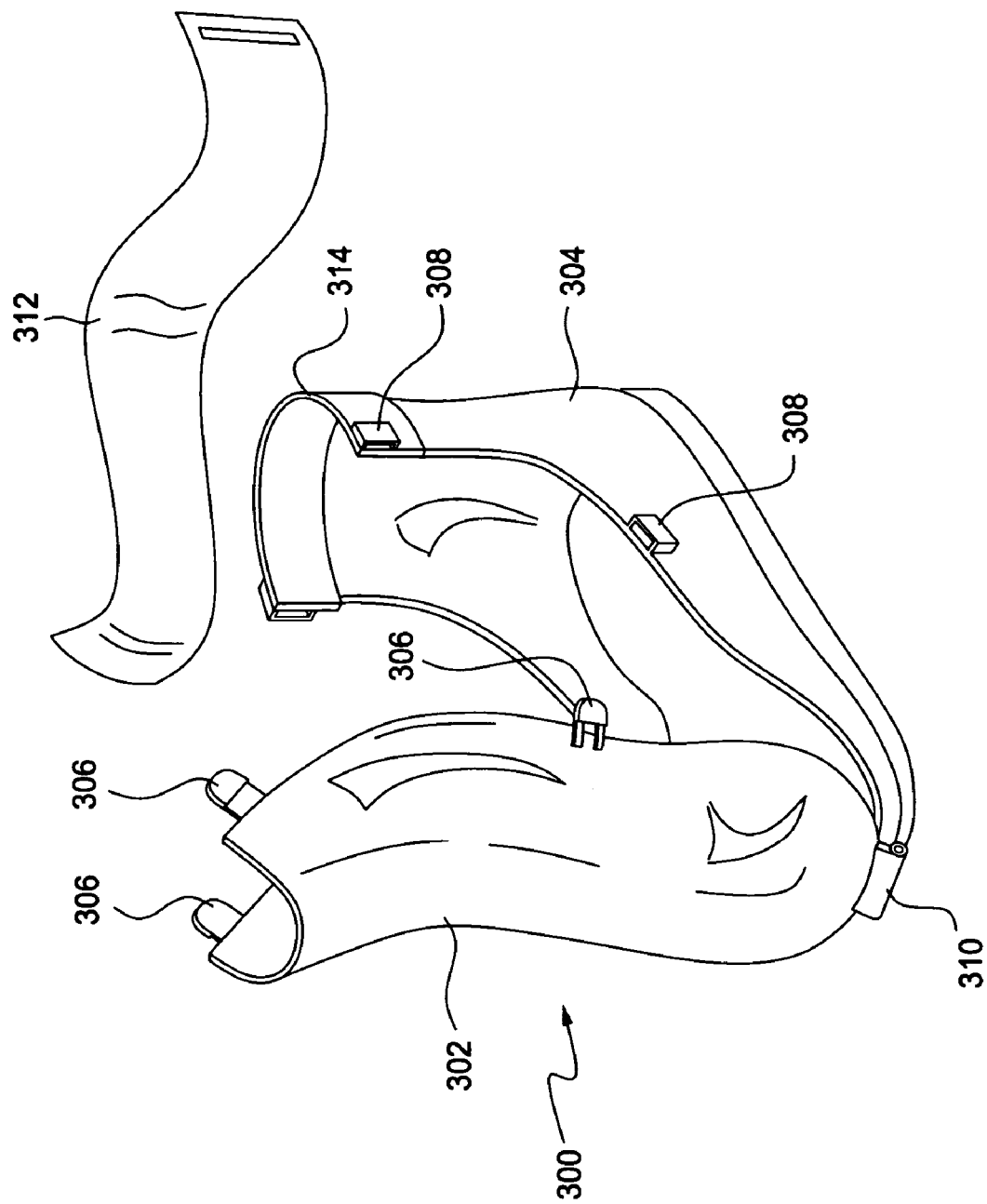
FIG. 22 is a perspective view of another embodiment of a negative pressure chamber in an open position.

FIG. 22 is a perspective view of an embodiment of a foot chamber (300). The foot chamber (300) comprises an upper housing (302) and a lower housing (304) that may be joined by a hinge (310). The upper housing (302) and lower housing (304) of the foot chamber (300) may also be joined by fasteners (306) on the upper housing (302) that engage with slots (308) in the lower housing (304) to secure the upper and lower housing to one another. An ankle seal (312) may be attached to the chamber (300) at the ankle opening (314) of the chamber (300).

Figure 23:
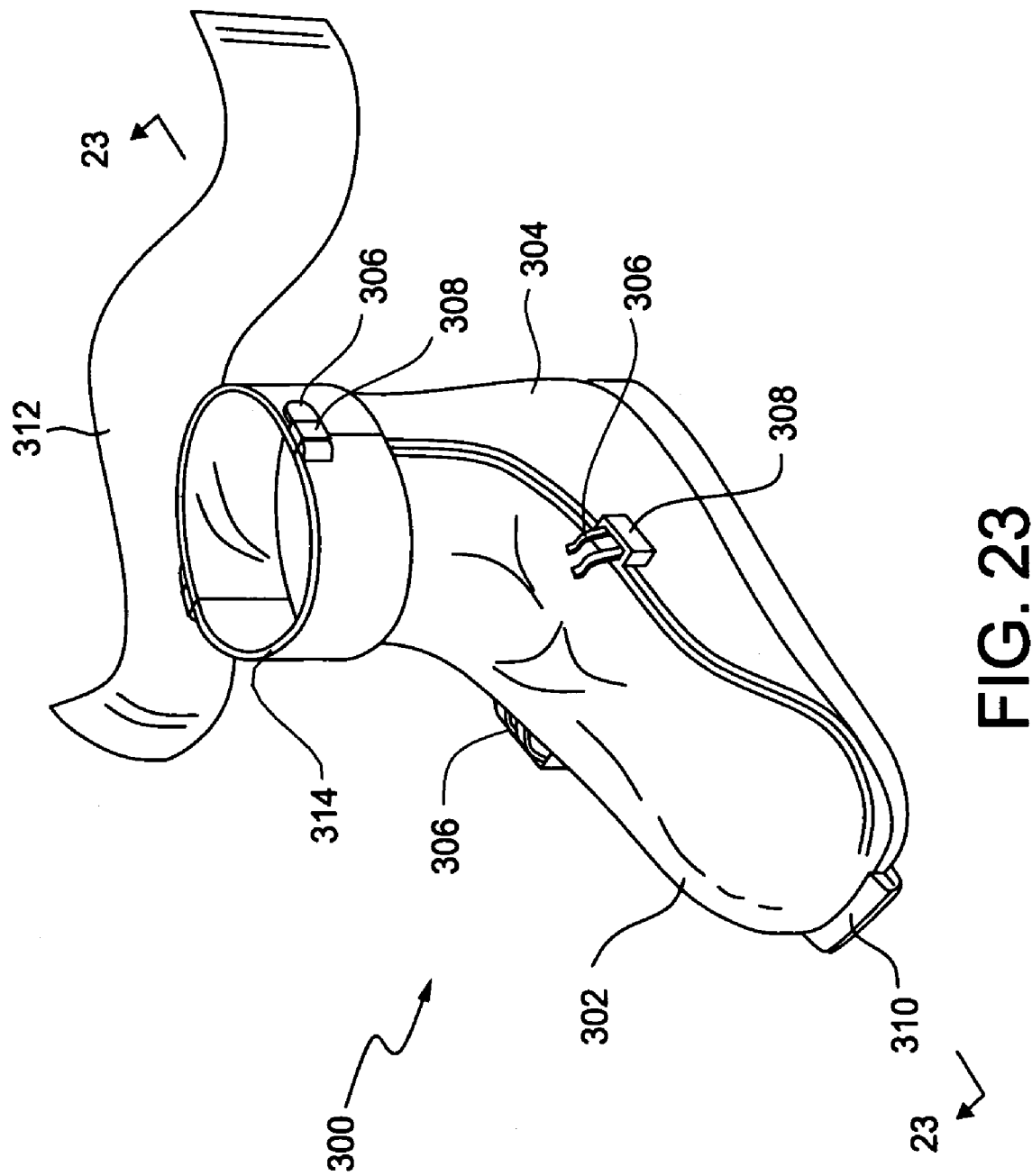
FIG. 23 is a perspective view of the negative pressure chamber of FIG. 22 in a closed position.
Figure 24:
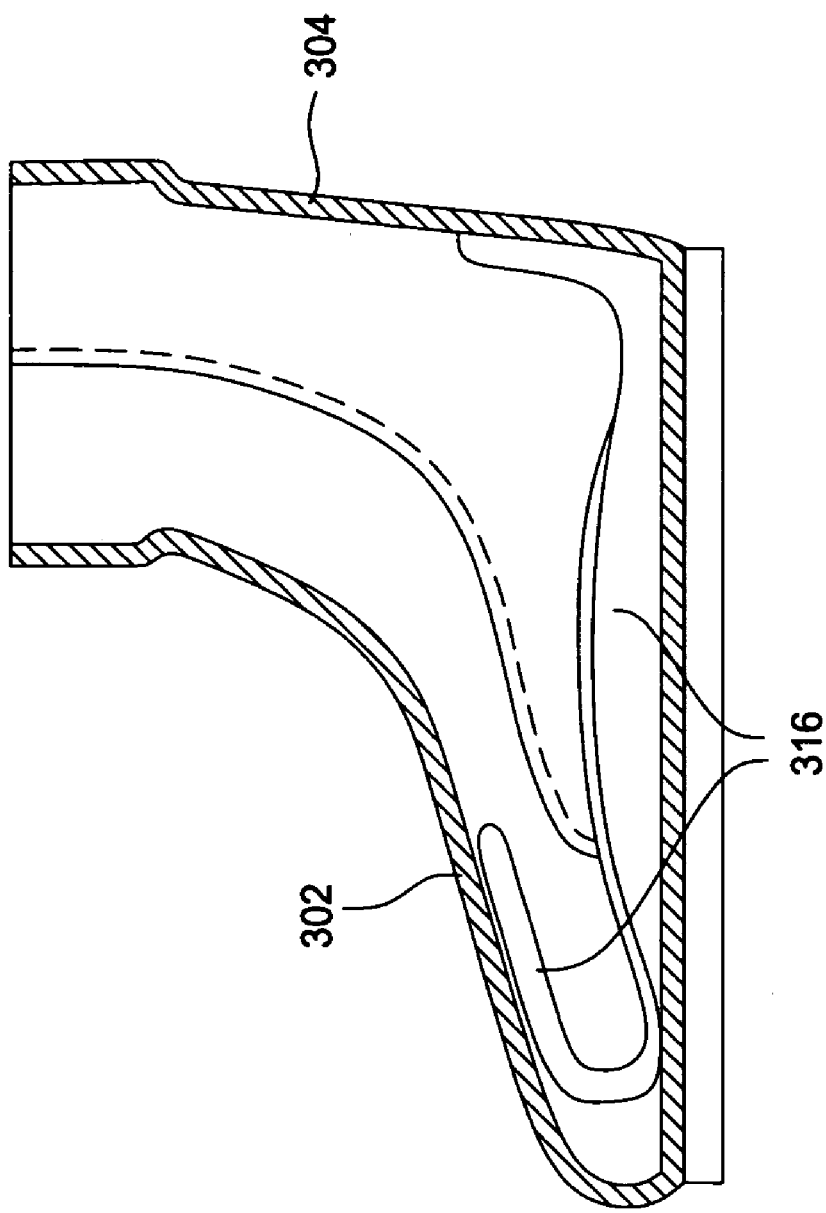
FIG. 24 is a cross-sectional view of the negative pressure chamber of FIG. 23.

FIG. 23 shows the foot chamber of FIG. 22 in a closed position. FIG. 23 is a cross-sectional view of the closed chamber (300) of FIG. 23 having a water heating pad (316) disposed therein. The water heating pad functions as a heat exchange element for a foot positioned in the foot chamber.

Figure 25:
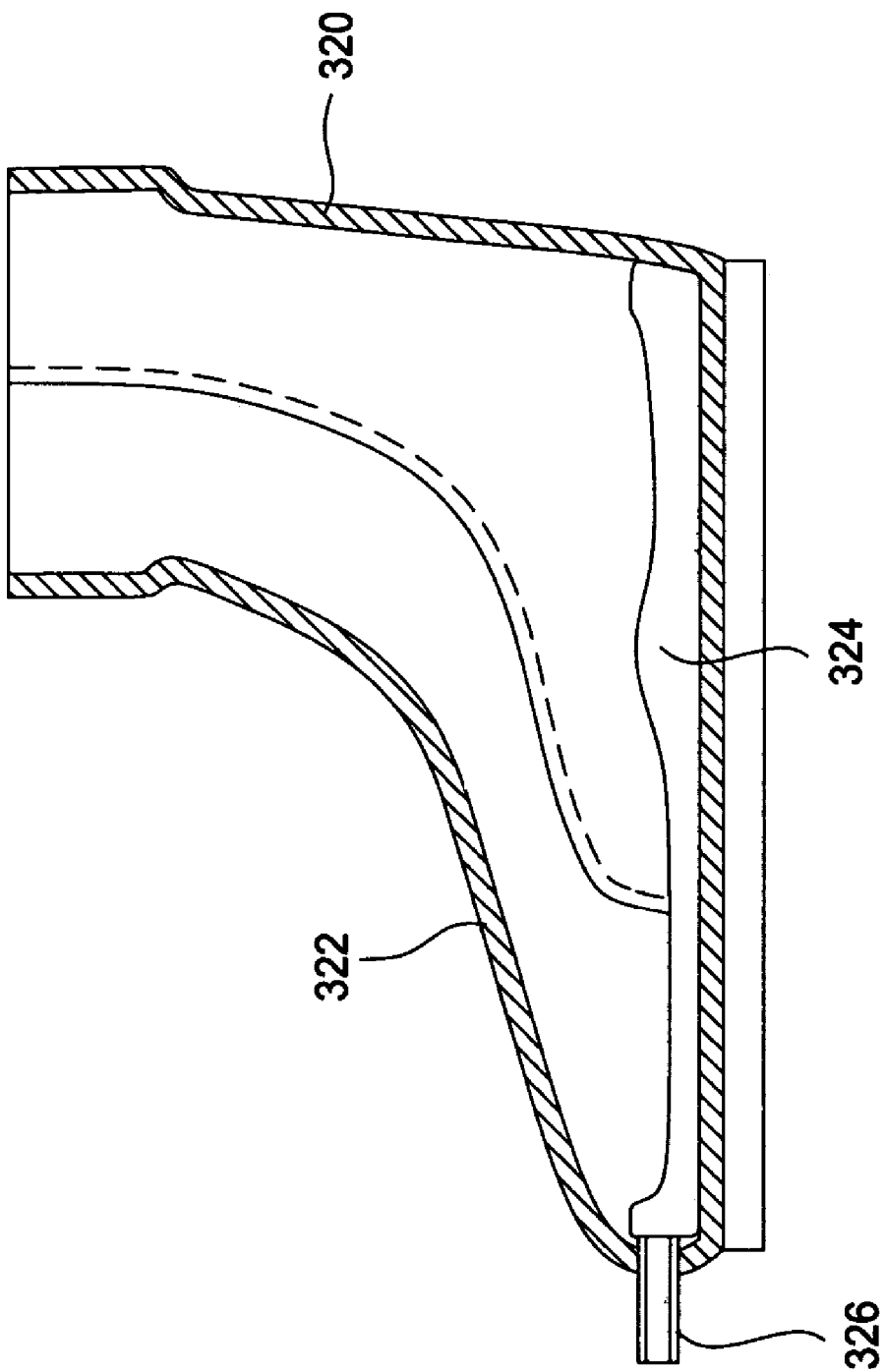
FIG. 25 is a cross-sectional view of another embodiment of a negative pressure chamber.

FIG. 25 is a cross-sectional view of another embodiment of a foot chamber having an upper housing (322) and a lower housing (320). A heat exchange element (324) is positioned in the lower housing (320) and is connected to a heat exchange medium source (not shown) via line (326), which may be a water tube.

The embodiments of the apparatus described above provide methods of adjusting body core temperature. In one embodiment, a suitable body appendage, preferably an appendage with the vasculature that may be vasodilated by the apparatus, such as a hand, may be placed into the lower portion of the chamber. The upper housing of the hand chamber may then be placed into alignment with the lower housing of the hand chamber and fastened shut by any of the methods previously described, thereby enclosing the hand. Alternatively, the hand may be placed into the upper housing of the chamber before the lower housing of the chamber. The interface between the hand and the hand opening may be sealed using a hand seal. The chamber with the sealed hand is placed over the heat exchange element and urged into sealable relation with the heat exchange element. Spring loaded indexed locking tongs secure the lower housing of the chamber to the heat exchange element. The chamber may also be attached to the heat exchange element using other techniques described herein.

In an alternative method, the heat exchange element may be urged into sealable relation with the lower housing of the chamber prior to placing the hand into the lower housing, placing the hand into the lower housing, applying the upper housing, and sealing the hand at the hand opening using a hand seal.

Prior to placing the hand in the chamber, a topical vasodilator, a heat conductive paste, or both may be applied to the hand, the heat exchange element, or the heat exchange element cover to facilitate heat conduction between the hand and the heat exchange element. For example, menthol is a topical vasodilator that may be used. Another topical vasodilator that may be used is methyl nicotinate. Such topical vasodilators may enhance the blood vessel dilation caused by the vacuum and thereby increase the heat exchange with the body core. The heat conductive paste may be any non-toxic, topical ointment or cream that is known to conduct heat.

Once the hand is enclosed in the chamber and the chamber is securely attached to the heat exchange element, negative pressure is applied to a vacuum port in the heat exchange element thereby lowering the pressure within the chamber and exposing the hand to decreased pressure in the range of −10 to −50 mm Hg, i.e., 10 to 50 mm Hg below the atmospheric pressure. Simultaneously or sequentially, the heat exchange medium is introduced into the heat exchange element. The flow rate of the vacuum pump may be greater than about 4 liters per minute, and preferably about 12 liters per minute or more. In one aspect, the flow rate of the vacuum pump is between about 4 liters and about 20 liters per minute and is preferably between about 12 and about 20 liters per minute to minimize leakage of the apparatus. The negative pressure also enhances the sealing of the apparatus by increasing the closing pressure on the seals between the parts of the apparatus and between the apparatus and the hand.

In one embodiment, a controller manipulates the heat exchange medium and negative pressure for the duration of the treatment, which may be about 30 minutes, for example. The duration may be longer or shorter depending on the size of the hand treated and the hand temperature, and may be repeated. The controller is configured to halt the treatment after each treatment period. A "stop" button on the control unit may be used to turn off both the heat exchange medium supply and the vacuum. Before a treatment is repeated, the health of the hand is examined. In certain embodiments, the upper housing of the chamber may be transparent to aid in the monitoring of the hand.

In one embodiment, the treatment may last for several hours, such as for the duration of a surgical procedure. The hand chamber may be opened during the surgical procedure to examine the condition of the hand.

Embodiments of the present invention may be used to maintain the body core temperature of a patient. Embodiments of the present invention may also be used for rapid re-warming of a patient. In such a method, the temperature of the heat exchange medium should be as high as possible without burning the patient. In a healthy patient, burning of the cells on the appendage can occur if the cell temperature exceeds approximately 43 degrees Celsius (° C.), but this may vary with exposure time and rate of heat transfer. Therefore, the temperature of the heat exchange medium is preferably calibrated such that skin temperature is less than 43 degrees Celsius.

In different embodiments, the heat exchange medium may be either a liquid or a gas. In practice, the heat exchange medium flow rate should be as high as possible, within practical limits of mechanics and noise. A high flow rate allows better temperature consistency, results in less heat loss, and creates better heat exchange. In a closed loop configuration including the heat exchange element and the heat exchange medium source, with a total system volume of 0.75 liters, a flow rate of 2 liters a minute transfers twice as much heat through the heat exchange element than a flow rate of 0.35 liters per minute.

Furthermore, the negative pressure is preferably as great as possible to maximize vasodilation, without restricting blood flow to the appendage. In tests with an external seal to the chamber with no sealing force on its own, the maximum negative pressure before a tourniquet effect was observed was in the range of −40 to −50 mm Hg. With a negative pressure of −35 mm Hg, a tourniquet effect was not observed. Generally, the apparatus may provide a negative pressure of about 0 to about −85 mm Hg, preferably a negative pressure of about 0 to about 45 mm Hg.

Higher levels of temperature and negative pressure may cause pain in some patients because of sensitivity to temperature and sensitivity to negative pressure. Additionally, sensitivity to temperature and negative pressure may be increased with extended treatment time or repeated treatments. Furthermore, some patients may be prone to petechia, a condition in which capillaries microburst under negative pressure. Consequently, in order to reduce patient discomfort, the controller may be configured with different temperature and vacuum settings. In one embodiment, one treatment setting is "High", which includes the highest temperature and negative pressure setting. "Medium" and "Low" settings have progressively lower settings for temperature and/or negative pressure. Patients who are at high risk for petechia or who are being treated for an extended amount of time may be treated on the "Low" setting. The vacuum setting may be adjusted to provide less negative pressure in patients that are under anesthesia since they are already vasodilated, while the heat is kept at a higher setting.

In one embodiment, the chamber with the enclosed hand is removed from the heat exchange element at the end of treatment. In an alternative embodiment, the hand is removed from the chamber before the chamber is detached from the heat exchange element.

In order to remove the hand from the chamber, the hand seal is typically unwrapped from the hand and the hand opening, and the upper portion and lower housing of the chamber are opened. In alternative embodiments, the hand may be removed from the chamber before the chamber is detached from the heat exchange element. The fasteners between the upper and lower portions of the chamber may unfasten easily, or they may be configured to break off when unfastened, limiting or preventing the future use of the chamber.

In one embodiment, as described above with respect to FIGS. 2, 3, and 3A, a spring loaded tong engagement mechanism may be used to separate the heat exchange element from the chamber. This quick release mechanism provides a safe and convenient means of disengaging the chamber from the heat exchange element in case treatment of the patient must be ended quickly. If reusable, the chamber may be attached to a different heat exchange element, such as to treat a patient in a different room if desired.

In a further aspect, embodiments of the invention provide a method of raising a body core temperature quickly with minimal energy consumption, as only a small portion of the body, i.e., the hand, is treated with heat and negative pressure. The apparatus may use between about 5 watts and about 250 watts to raise a body core temperature at a rate of between about 4° C./hour and about 12° C./hour. Preferably, the power applied is between about 5 watts and about 80 watts, although a power of up to about 250 watts may be used to heat large areas of a body, such as both arms and legs. In contrast, a convective warming blanket that heats the whole body may use about 500 watts.

In yet another embodiment, a method of regulating a body core temperature includes exposing one or more extremities of a body to negative pressure and heating a region of the body adjacent the one or more extremities. The extremities themselves may also be heated. The region of the body that is heated may have a greater surface area than the surface area of the one or more extremities. Thus, in one aspect, the area of the surface that receives negative pressure treatment is not the same as the area of the surface that receives heat treatment.

The one or more extremities may be fingers or toes. When using fingers as the treated extremities, the region of an arm from the elbow to the fingers may be used as the region adjacent the extremities. When using toes as the treated extremities, the region of a foot from the toes to the knee may be used as the region adjacent the extremities. It is believed that as the extremities are more responsive to the application of negative pressure than appendages as a whole, substantially the same vasodilation achieved by treating an appendage with negative pressure may be achieved by applying negative pressure only to the extremities of the appendage. Thus, the surface area of the patient that is exposed to negative pressure is minimized.

Figure 26:
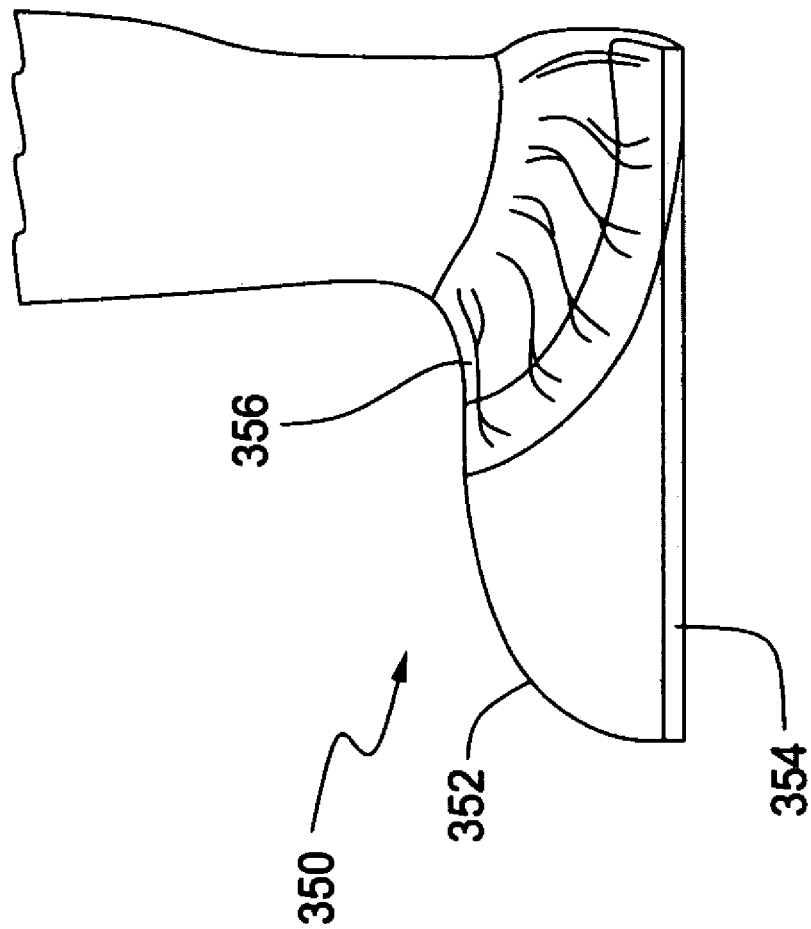
FIG. 26 is a perspective view of another embodiment of a negative pressure chamber having a portion of a foot disposed therein.

An example of an apparatus for treating toes as described above is shown in FIG. 26. The apparatus (350) includes a housing (352) that is adapted to cover a portion of a foot including the toes but does not cover an entire foot. Seal (356) attaches the chamber (350) to the foot. A heat exchange element (354) may be attached to a lower portion of the housing (352), as shown in FIG. 26, or may be positioned within the housing (352). The apparatus (350) also include vacuum ports (not shown) such that a portion of a foot enclosed within apparatus may be exposed to a negative pressure environment. A foot may be positioned on the heat exchange element such that heat is provided along the length of the foot, i.e., from the toes of the foot to the heel of the foot. Thus, such an apparatus provides a method of exposing toes to negative pressure while heating both the toes and parts of the foot that are not exposed to negative pressure.

While the foregoing is directed to embodiments of the present invention, other and further embodiments of the invention may be devised without departing from the basic scope thereof, and the scope thereof is determined by the claims that follow.

What is claimed is:

1. An apparatus for regulating a body core temperature, comprising:
   a heat exchange element; and
   an appendage chamber adapted to be disassembled from the heat exchange element and having an appendage seal attached thereon, the appendage chamber comprising:
      an upper housing and a lower housing, wherein a lower surface of the upper housing of the chamber is attached to an upper surface of the lower housing of the chamber, and a lower surface of the lower housing of the chamber is attached to an upper surface of the heat exchange element;
      a first gasket between the lower surface of the upper housing of the chamber and the upper surface of the lower housing of the chamber; and
      a second gasket between the lower surface of the lower housing of the chamber and the upper surface of the heat exchange element.

2. The apparatus of claim 1, wherein the appendage chamber is disposable.

3. The apparatus of claim 1, wherein the appendage chamber comprises an acrylic material.

4. The apparatus of claim 1, wherein the heat exchange element comprises one or more protruding portions that are received by one or more recessed regions in the appendage chamber such that the heat exchange element and the appendage chamber are attached.

5. The apparatus of claim 4, wherein the heat exchange element comprises an actuator adapted to retract the one or more protruding portions of the heat exchange element from the one or more recessed regions in the appendage chamber.

6. The apparatus of claim 1, wherein the heat exchange element comprises a vacuum port and a vacuum sensor port.

7. The apparatus of claim 1, wherein the heat exchange element is attached to a source of a heat exchange medium in a closed loop configuration.

8. The apparatus of claim 1, wherein the lower housing defines an aperture adapted to receive a portion of the heat exchange element therethrough.

9. An apparatus for regulating a body core temperature, comprising:
   a heat exchange element; and
   an appendage chamber having an appendage seal attached thereon, the appendage chamber comprising an upper housing and a tower housing, wherein the upper housing comprises a strap adapted to hold an appendage disposed in the apparatus on the heat exchange element, and wherein the appendage chamber is adapted to be disassembled from the heat exchange element.

10. The apparatus of claim 9, wherein the appendage chamber is disposable.

11. The apparatus of claim 9, wherein the appendage chamber comprises an acrylic material.

12. The apparatus of claim 9, wherein the heat exchange element comprises one or more protruding portions that are received by one or more recessed regions in the appendage chamber such that the heat exchange element and the appendage chamber are attached.

13. The apparatus of claim 12, wherein the heat exchange element further comprises an actuator adapted to retract the one or more protruding portions of the heat exchange element from the one or more recessed regions in the appendage chamber.

14. The apparatus of claim 9, wherein the heat exchange element comprises a vacuum port and a vacuum sensor port.

15. The apparatus of claim 9, wherein the heat exchange element is attached to a source of a heat exchange medium in a closed loop configuration.

16. The apparatus of claim 9, wherein the lower housing defines an aperture adapted to receive a portion of the heat exchange element therethrough.

17. An apparatus for regulating a body core temperature, comprising:
   a heat exchange element, wherein the heat exchange element maintains an impression of a hand to hold an appendage disposed in the apparatus on the heat exchange element; and
   an appendage chamber having an appendage seal attached thereon, wherein the appendage chamber is adapted to be disassembled from the heat exchange element, and the appendage chamber comprises an upper housing and a lower housing.

18. The apparatus of claim 17, wherein the appendage chamber is disposable.

19. The apparatus of claim 17, wherein the appendage chamber comprises an acrylic material.

20. The apparatus of claim 17, wherein the heat exchange element comprises one or more protruding portions that are received by one or more recessed regions in the appendage chamber such that the heat exchange element and the appendage chamber are attached.

21. The apparatus of claim 20, wherein the heat exchange element further comprises an actuator adapted to retract the one or more protruding portions of the heat exchange element from the one or more recessed regions in the appendage chamber.

22. The apparatus of claim 17, wherein the heat exchange element comprises a vacuum port and a vacuum sensor port.

23. The apparatus of claim 17, wherein the heat exchange element is attached to a source of a heat exchange medium in a closed loop configuration.

24. The apparatus of claim 17, wherein the lower housing defines an aperture adapted to receive a portion of the heat exchange element therethrough.

25. An apparatus for regulating a body core temperature, comprising:
   a heat exchange element, wherein the heat exchange element is coated with a substance with adhesive properties to hold an appendage thereon; and
   an appendage chamber having an appendage seal attached thereon, wherein the appendage chamber is adapted to be disassembled from the heat exchange element, and the appendage chamber comprises an upper housing and a lower housing.

26. The apparatus of claim 25, wherein the appendage chamber is disposable.

27. The apparatus of claim 25, wherein the appendage chamber comprises an acrylic material.

28. The apparatus of claim 25, wherein the heat exchange element comprises one or more protruding portions that are received by one or more recessed regions in the appendage chamber such that the heat exchange element and the appendage chamber are attached.

29. The apparatus of claim 28, wherein the heat exchange element comprises an actuator adapted to retract the one or more protruding portions of the heat exchange element from the one or more recessed regions in the appendage chamber.

30. The apparatus of claim 25, wherein the heat exchange element comprises a vacuum port and a vacuum sensor port.

31. The apparatus of claim 25, wherein the heat exchange element is attached to a source of a heat exchange medium in a closed loop configuration.

32. The apparatus of claim 25, wherein the lower housing defines an aperture adapted to receive a portion of the heat exchange element therethrough.

33. A method of regulating a body core temperature, comprising:
   deploying an appendage chamber from a collapsed state;
   placing an appendage in an apparatus comprising the appendage chamber having an appendage seal attached thereon and a heat exchange element;
   heating the appendage; and
   exposing the appendage to negative pressure.

34. The method of claim 33, wherein the negative pressure is between about 0 and about 85 mm Hg below ambient pressure.

35. A method of regulating a body core temperature, comprising:
   applying a heat conductive paste to an appendage;
   placing the appendage in an apparatus comprising an appendage chamber having an appendage seal attached thereon and a heat exchange element;
   heating the appendage; and
   exposing the appendage to negative pressure.

36. The method of claim 35, wherein the negative pressure is between about 0 and about 85 mm Hg below ambient pressure.

37. A method of regulating a body core temperature, comprising:
   applying a topical vasodilator to an appendage;

placing the appendage in an apparatus comprising an appendage chamber having an appendage seal attached thereon and a heat exchange element;
heating the appendage; and
exposing the appendage to negative pressure.

38. The method of claim 37, wherein the negative pressure is between about 0 and about 85 mm Hg below ambient pressure.

* * * * *

UNITED STATES PATENT AND TRADEMARK OFFICE
CERTIFICATE OF CORRECTION

| | | |
|---|---|---|
| PATENT NO. | : 7,160,316 B2 | Page 1 of 1 |
| APPLICATION NO. | : 10/948121 | |
| DATED | : January 9, 2007 | |
| INVENTOR(S) | : Hamilton et al. | |

It is certified that error appears in the above-identified patent and that said Letters Patent is hereby corrected as shown below:

In Section (56) References Cited:

On the Title Page, in the U.S. Patent Documents, please delete "5,478,490" and insert --5,476,490--.

In the Specification:

In Column 6, Line 6, please delete "housing.(3)" and insert --housing (3)--;

In Column 6, Line 32, please "the," and insert --the--;

In Column 11, Line 58, please delete "cover-vacuum" and insert --cover vacuum--;

In Column 19, Line 4, please delete "45" and insert -- -45--.

In the Claims:

In Column 21, Claim 9, Line 18, please delete "tower" and insert --lower--.

Signed and Sealed this

Tenth Day of July, 2007

JON W. DUDAS
*Director of the United States Patent and Trademark Office*